(12) United States Patent
Townsend et al.

(10) Patent No.: US 7,507,259 B2
(45) Date of Patent: Mar. 24, 2009

(54) PROSTHETIC FOOT WITH TUNABLE PERFORMANCE

(75) Inventors: Barry W. Townsend, Bakersfield, CA (US); Byron Kent Claudino, Bakersfield, CA (US)

(73) Assignee: Bioquest Prosthetics, LLC, Bakersfield, CA (US)

( * ) Notice: Subject to any disclaimer, the term of this patent is extended or adjusted under 35 U.S.C. 154(b) by 375 days.

(21) Appl. No.: 10/473,682

(22) PCT Filed: Mar. 29, 2002

(86) PCT No.: PCT/US02/09589

§ 371 (c)(1),
(2), (4) Date: Sep. 30, 2003

(87) PCT Pub. No.: WO02/078578

PCT Pub. Date: Oct. 10, 2002

(65) Prior Publication Data

US 2004/0117036 A1    Jun. 17, 2004

Related U.S. Application Data

(63) Continuation-in-part of application No. 09/820,895, filed on Mar. 30, 2001, now Pat. No. 6,562,075.

(51) Int. Cl.
*A61F 2/66* (2006.01)
(52) U.S. Cl. .............................. 623/52; 623/47; 623/53; 623/55
(58) Field of Classification Search .............. 623/47–55
See application file for complete search history.

(56) References Cited

U.S. PATENT DOCUMENTS 640,540 A    1/1900    Daniels
(Continued)

FOREIGN PATENT DOCUMENTS

CA    2103341 A1    4/1995
(Continued)

OTHER PUBLICATIONS

PCT Written Opinion from International Application No: PCT/US02/06901.
(Continued)

*Primary Examiner*—Dave Willse
*Assistant Examiner*—Javier G Blanco
(74) *Attorney, Agent, or Firm*—Antonelli, Terry, Stout & Kraus, LLP.

(57) ABSTRACT

A prosthetic foot (70) incorporates a foot keel (77) and a calf shank (72) connected to the foot keel to form an ankle joint area of the prosthetic foot. The foot keel has forefoot and hindfoot portions and an upwardly arched midfoot portion extending between the forefoot and midfoot portions. The calf shank includes a downward convexly curved lower end which is adjustably attached at a portion thereof to the foot keel by way of a releasable fastener arrangement. The upper end of the calf shank is movable longitudinally of the foot keel in response to force loading and unloading the calf shank during use of the prosthetic foot. A device (71) connected between the ends of the calf shank limits the extent of the motion of the upper end of the calf shank relative to the lower end and foot keel. The upper end of the calf shank can include an alignment coupler device (92) thereon having adjustable slide mechanisms to adjust the medial/lateral and anterior/posterior position of the calf shank relative to a supporting structure on the leg of the person using the prosthetic foot.

68 Claims, 16 Drawing Sheets

U.S. PATENT DOCUMENTS

| | | | |
|---|---|---|---|
| 810,180 | A | 1/1906 | Wintermute |
| 2,453,969 | A * | 11/1948 | Carter .......................... 623/52 |
| 3,335,428 | A | 8/1967 | Gajdos |
| 4,555,817 | A | 12/1985 | McKendrick |
| 4,645,509 | A | 2/1987 | Poggie et al. |
| 4,721,510 | A | 1/1988 | Cooper et al. |
| 4,822,363 | A | 4/1989 | Phillips |
| 4,892,554 | A | 1/1990 | Robinson |
| 4,911,724 | A | 3/1990 | Fikes |
| 4,938,776 | A | 7/1990 | Masinter |
| 4,959,073 | A | 9/1990 | Merlette |
| 4,994,086 | A | 2/1991 | Edwards |
| 5,019,109 | A | 5/1991 | Voisin |
| 5,062,859 | A | 11/1991 | Naeder |
| 5,066,305 | A | 11/1991 | Firth |
| 5,112,356 | A | 5/1992 | Harris et al. |
| 5,116,383 | A | 5/1992 | Shorter et al. |
| 5,139,525 | A | 8/1992 | Kristinsson |
| 5,156,632 | A | 10/1992 | Wellershaus |
| 5,181,932 | A | 1/1993 | Phillips |
| 5,181,933 | A | 1/1993 | Phillips |
| 5,219,365 | A | 6/1993 | Sabolich |
| 5,258,039 | A | 11/1993 | Goh et al. |
| 5,290,319 | A | 3/1994 | Phillips |
| 5,312,669 | A | 5/1994 | Bedard |
| 5,314,499 | A | 5/1994 | Collier, Jr. |
| 5,376,133 | A | 12/1994 | Gramnas |
| 5,376,139 | A | 12/1994 | Pitkin |
| 5,376,141 | A | 12/1994 | Phillips |
| 5,387,246 | A | 2/1995 | Phillips |
| 5,443,522 | A | 8/1995 | Hiemisch |
| 5,443,527 | A | 8/1995 | Wilson |
| 5,458,656 | A | 10/1995 | Phillips |
| 5,482,513 | A | 1/1996 | Wilson |
| 5,486,209 | A | 1/1996 | Phillips |
| 5,507,838 | A | 4/1996 | Chen |
| 5,509,936 | A | 4/1996 | Rappoport et al. |
| 5,509,937 | A | 4/1996 | Allard et al. |
| 5,509,938 | A | 4/1996 | Phillips |
| 5,514,185 | A | 5/1996 | Phillips |
| 5,545,230 | A | 8/1996 | Kinsinger et al. |
| 5,549,714 | A | 8/1996 | Phillips |
| 5,571,213 | A | 11/1996 | Allen |
| 5,593,456 | A | 1/1997 | Merlette |
| 5,593,457 | A | 1/1997 | Phillips |
| 5,653,767 | A | 8/1997 | Allen et al. |
| 5,653,768 | A | 8/1997 | Kania |
| 5,695,526 | A | 12/1997 | Wilson |
| 5,695,527 | A | 12/1997 | Allen |
| 5,702,488 | A | 12/1997 | Wood et al. |
| 5,725,598 | A | 3/1998 | Phillips |
| 5,728,176 | A | 3/1998 | Phillips |
| 5,728,177 | A | 3/1998 | Phillips |
| 5,746,773 | A | 5/1998 | Littig |
| 5,766,264 | A | 6/1998 | Lundt |
| 5,776,205 | A | 7/1998 | Phillips |
| 5,800,568 | A | 9/1998 | Atkinson et al. |
| 5,800,569 | A | 9/1998 | Phillips |
| 5,824,112 | A | 10/1998 | Phillips |
| 5,897,594 | A | 4/1999 | Martin et al. |
| 5,899,944 | A | 5/1999 | Phillips |
| 5,944,760 | A | 8/1999 | Christensen |
| 5,976,191 | A | 11/1999 | Phillips |
| 5,993,488 | A | 11/1999 | Phillips |
| 6,051,026 | A | 4/2000 | Biedermann et al. |
| 6,071,313 | A | 6/2000 | Phillips |
| 6,077,301 | A | 6/2000 | Pusch |
| 6,083,265 | A | 7/2000 | Shorter et al. |
| 6,099,572 | A | 8/2000 | Mosler et al. |
| 6,187,052 | B1 | 2/2001 | Molino et al. |
| 6,197,066 | B1 | 3/2001 | Gabourie |
| 6,206,932 | B1 | 3/2001 | Johnson |
| 6,206,934 | B1 | 3/2001 | Phillips |
| 6,228,043 | B1 | 5/2001 | Townsend et al. |
| 6,241,776 | B1 | 6/2001 | Christensen |
| 6,270,468 | B1 | 8/2001 | Townsend et al. |
| 6,280,479 | B1 | 8/2001 | Phillips |
| 6,290,730 | B1 | 9/2001 | Pitkin et al. |
| 6,350,286 | B1 | 2/2002 | Atkinson et al. |
| 6,402,790 | B1 | 6/2002 | Celebi |
| 6,406,500 | B1 | 6/2002 | Phillips |
| 6,443,995 | B1 | 9/2002 | Townsend et al. |
| 6,514,293 | B1 | 2/2003 | Jang et al. |
| 6,527,811 | B1 | 3/2003 | Phillips |
| 6,562,075 | B2 | 5/2003 | Townsend et al. |
| 6,602,295 | B1 | 8/2003 | Doddroe et al. |
| 6,663,673 | B2 | 12/2003 | Christensen |
| 2002/0040249 | A1 | 4/2002 | Phillips |
| 2002/0077706 | A1 | 6/2002 | Phillips |
| 2002/0087216 | A1 | 7/2002 | Atkinson et al. |
| 2002/0116072 | A1 | 8/2002 | Rubie et al. |
| 2002/0133237 | A1 | 9/2002 | Christesen |
| 2003/0009238 | A1 | 1/2003 | Whayne |
| 2003/0028256 | A1 | 2/2003 | Townsend et al. |
| 2003/0045944 | A1 | 3/2003 | Mosler et al. |
| 2003/0093158 | A1 | 5/2003 | Phillips et al. |
| 2003/0120354 | A1 | 6/2003 | Doddroe et al. |
| 2003/0191540 | A1 | 10/2003 | Townsend et al. |

FOREIGN PATENT DOCUMENTS

| | | |
|---|---|---|
| DE | 325171 C1 | 10/1920 |
| DE | 19717298 C1 | 5/1998 |
| DE | 298 20 904 U1 | 6/1999 |
| DE | 298 23 435 U1 | 9/1999 |
| DE | 29920434 U1 | 5/2000 |
| DK | EP 0 648 479 A1 | 10/1993 |
| EP | 0 331 468 | 9/1989 |
| EP | 0 648 479 A1 | 4/1995 |
| EP | 0793949 A1 | 9/1997 |
| FR | 2 640 499 A1 | 6/1990 |
| FR | 2 734 151 | 11/1996 |
| FR | 2734151 | 11/1996 |
| GB | 2 173 569 | 10/1986 |
| JP | 9-327473 | 12/1997 |
| JP | 11-299815 | 11/1999 |
| WO | WO 91/00070 | 1/1991 |
| WO | WO 94/10942 | 5/1994 |
| WO | WO 97/17042 | 5/1997 |
| WO | WO 00/71061 A1 | 11/2000 |
| WO | WO 02/02034 A1 | 1/2002 |
| WO | WO 02/30340 | 4/2002 |

OTHER PUBLICATIONS

International Search Report from International Application No. PCT/US01/48954.

International Search Report (Apr. 2002); International application No. PCT/US02/09573.

International Search Report (Jul. 1998); International application No. PCT/US02/30471.

Perry J. and Shanfield S., *Efficiency of Dynamic Elastic Response Prosthetic Feet; Gait Initiation in Below-Knee Amputees: Analysis of Safe Function; Biomechanical Evaluation of Energy-Storing Prosthetic Feet*, J. Rehabilitation Research and Development Service (Project #A517-RA), 1990, pp. 37, 38 & 44.

Barth, D.G., Schumacher, L. and Thomas, S.S., *Gait Analysis and Energy Cost of Below-Knee Amputees Wearing Six Different Prosthetic Feet*, JPO: Journal of Prosthetics and Orthotics, 1992, vol. 4, No. 2, pp. 626-638.

Menard, M.R. and Murray D.D., *Subjective and Objective Analysis of an Energy-Storing Prosthetic Foot*, Journal of Prosthetics and Orthotics, 1989, vol. 1, No. 4, pp. 173-183.

Menard, M.R., McBride, M.E., Sanderson, D.J. and Murray, D.D., *Comparative Biomechanical Analysis of Energy-Storing Prosthetic Feet*, Archives of Physical Medicine and Rehabilitation, May 1992, vol. 73, pp. 451-458.

Prince, F., Winter, D.A. et al., *Mechanical Efficiency During Gait of Adults with Transtibial Amputation: A Pilot Study Comparing the SACH, Seattle, and Golden-Ankle Prosthetic Feet*, Journal of Rehabilitation Research and Development, Jun. 1998, vol. 35, No. 2, pp. 177-185.

Winter, D.A., *Biomechanics of Human Movement*, John Wiley & Sons, Inc., 1979, pp. 61, 117-121.

Mann, R.A. and Hagy, J.L., *The Function of the Toes in Walking, Jogging and Running*, J.J.B. Lippincott Company, 1979, vol. 142, pp. 24-29.

Perry, J., *Gait Analysis: Normal and Pathological Function*, SLACK Incorporated, Thorofare, NJ, 1992, Chapter 4: *Ankle Foot Complex*, Chapter 19: *Ground Reaction Force and Vector Analysis*, Chapter 21: *Energy Expenditure*.

Valmassy, R.L., *Clinical Biomechanics of the Lower Extremities*, Mosby, 1996, Chapter 1: *Lower Extremity Function and Normal Mechanics*.

Hsu, M. and Nielsen, D., et al., *Physiological Measurements of Walking and Running in People with Transtibial Amputations With 3 Different Prostheses*, Journal of Othopaedic & Sports Physical Therapy, Sep. 1999; vol. 29, No. 9, pp. 527-533.

Macfarlane, P.A. and Nielsen, D.H. et al., *Gait Comparisons for Below-Knee Amputees Using a Flex-Foot™ Versus a Conventional Prosthetic Foot*, Journal of Prosthetics and Orthotics, 1991, vol. 3, No. 4, pp. 526-537.

Neilson, D.H. and Shurr, D.G. et al., *Comparison of Energy Cost and Gait Efficiency During Ambulation in Below-Knee Amputees Using Different Prosthetic Feet—A Preliminary Report*, Journal of Prosthetics and Orthotics, 1988, vol. 1, No. 1, pp. 24-31.

Macfarlane, P.A. and Nielsen, D.H. et al., *Perception of Walking Difficulty by Below-Knee Amputees Using a Conventional Foot Versus the Flex-Foot*, Journal of Prosthetics and Orthotics, 1991, vol. 3, No. 3., pp. 503-508.

Childress, D., *Mechanical Properties of Prosthetic and Human Feet: From Shoes to Computer Alignment*, 2nd Conference of Advanced Prosthetics, Apr. 2002.

Wirta, R.W. et al., *Effect on Gait Using Various Prosthetic Ankle-Foot Devices*, Journal of Rehabilitation Research and Development, 1991, vol. 28, No. 2, pp. 13-24.

Winter, D.A. and Patia A.E. et al., *Biomechanical Walking Pattern Changes in the Fit and Healthy Elderly*, Physical Therapy, Jun. 1990, vol. 70, No. 6, pp. 340/15-346/21.

Ayyappa, E., *Normal Human Locomotion, Part 1: Basic Concepts and Terminology*, Journal of Prosthetics and Orthotics, Winter 1997, vol. 9, No. 1, pp. 10-17.

Ayyappa, E., *Normal Human Locomotion, Part 2: Motion, Ground-Reaction Force and Muscle Activity*, Journal of Prosthetics and Orthotics, Spring 1997, vol. 9, No. 2, pp. 49-57.

Winter, D.A., *Biomechanics and Motor Control of Human Movement*, University of Waterloo, John Wiley & Sons, Inc., 1990, Chapter 7.

J.B. Saunders, et al., *The Major Determinants in Normal and Pathological Gait*, Journal of Bone and Joint Survey, Jul. 1953, vol. 35A, No. 3, pp. 543-558.

Komi, P.V., *Strength and Power in Sport*, Blackwell Scientific Publications, 1992, Chapter 6B, pp. 115-129.

McComas, A.J., *Skeletal Muscle Form and Function*, Human Kinetics, Champaign, IL, 1996, pp. 326-375.

Mattes, S.J., et al., *Walking Symmetry and Energy Cost in Persons with Unilateral Transtibial Amputations: Matching Prosthetic and Intact Limb Inertial Properties*, Archives of Physcial Medicine and Rehabilitation, May 2000, vol. 81, pp. 561-568.

Bojsen-Moller, F., *Calcaneocuboid Joint and Stability of the Longitudinal Arch of the Foot at High and Low Gear Push Off*, Journal of Anatomy, Aug.-Dec. 1979, vol. 129, pp. 165-176.

Hicks, J.H., *The Mechanics of the Foot, The Plantar Aponeurosis and the Arch*, Journal of Anatomy, 1954, vol. 88, Pt. 1, pp. 25-31.

Brunnstrom, S. (revised by R. Dickinson), *Clinical Kinesiology*, F.A. Davis Company, Philadelphia, 1972, pp. 35.

Stiehl, J., *Inman's Joints of the Ankle*(2nd Ed.). Williams & Wilkins, Baltimore, MD, 1991, p. 39.

Bateni, H., et al., *Kinematic and Kinetic Variations of Below-Knee Amputee Gait*, Prosthetic and Orthotic Science, 2002, vol. 14, No. 1, pp. 2-10.

International Search Report; PCT/US03/09506; filed Mar. 31, 2003.

2003 Ossur Product Catalog; TALUX™; pp. 179-181.

International Search Report; PCT/US05/11304; Filing Date: Apr. 1, 2005.

International Search Report; PCT/US05/11291; Filing Date: Apr. 1, 2005.

Supplementary Partial European Search Report; EP 02 75 7836; Date: Mar. 7, 2006.

Supplementary Partial European Search Report; EP 02 71 3785; Date: Mar. 7, 2006.

International Search Report; PCT/US05/34037; Filing Date: Sep. 26, 2005.

Supplementary European Search Report; EP 02 71 3785; May 22, 2006.

Supplementary European Search Report; EP 02 75 7836; May 25, 2006.

Japanese Office Action; Patent Application No. 576848/2002; pp. 1-4 and English translation of the Japanese Office Action.

European Office Action: Application No. 02 757 836.8-2310; 5 pages; Owner; Barry w. Townsend, et al.; Title: Prosthetic Foot With Tunable Performance, dated Jul. 31, 2008.

European Office Action: Application No. 02 713 785.0-2310; 5 pages; Owner: Barry w. Townsend, et al.; Title: Prosthetic Foot With Tunable Performance.

* cited by examiner

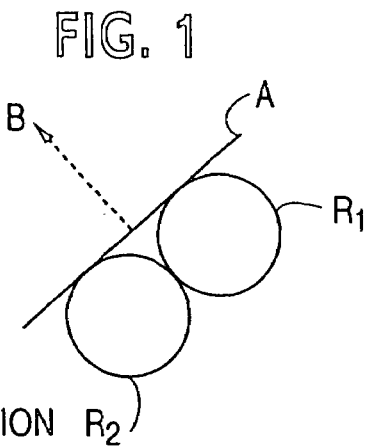
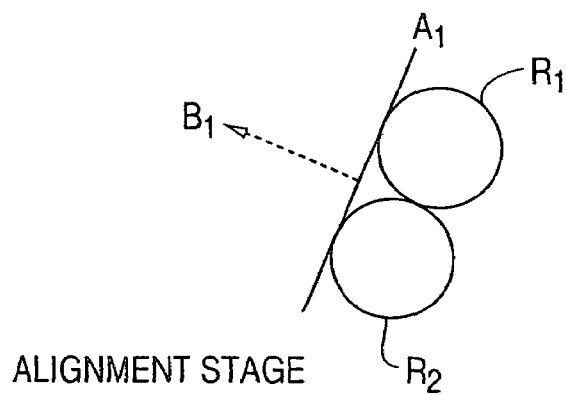
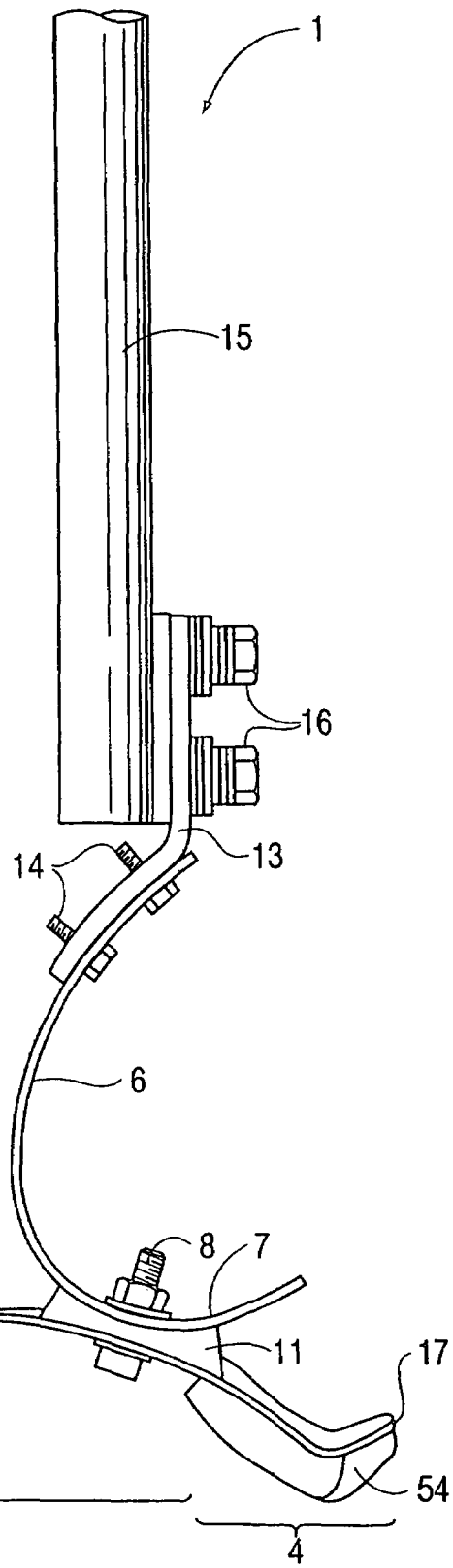

FIG. 4
FIG. 5
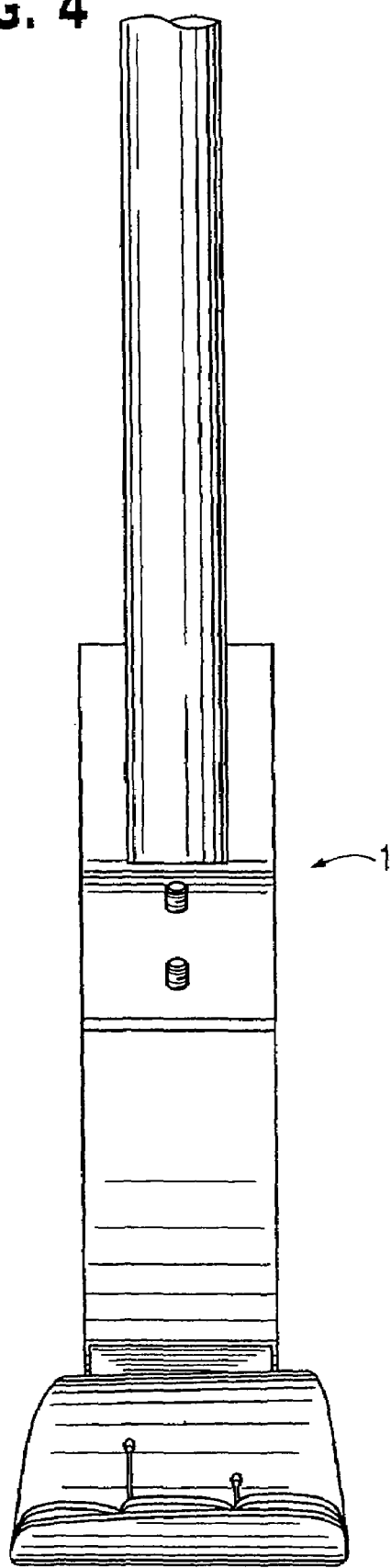
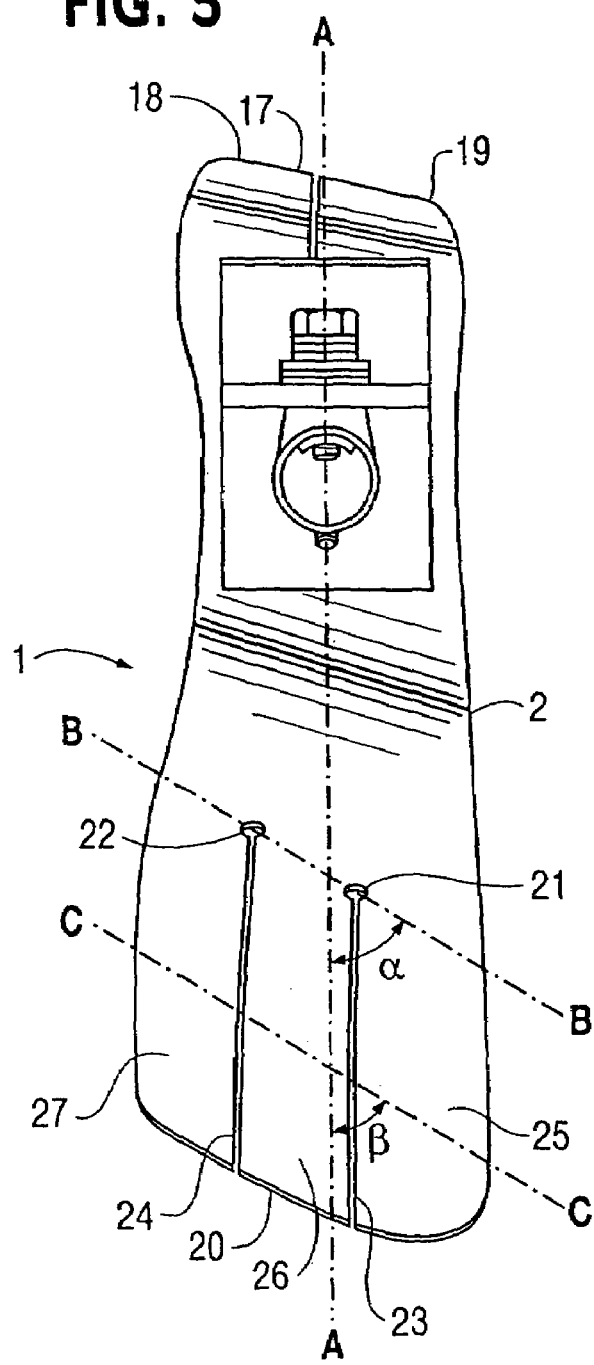

42

43

44
10

10
45

46

47

48

49

PROSTHETIC FOOT WITH TUNABLE PERFORMANCE

RELATED APPLICATIONS

This application is a U.S. national designated filing under 35 U.S.C. §371 of international application PCT/US02/09589 filed Mar. 29, 2002, which is a continuation in part of U.S. application Ser. No. 09/820,895, filed Mar. 30, 2001 and now U.S. Pat. No. 6,562,075 issued May 13, 2003, the priority of which is claimed.

TECHNICAL FIELD

The present invention relates to a high performance prosthetic foot providing improved dynamic response capabilities as these capabilities relate to applied force mechanics.

BACKGROUND ART

A jointless artificial foot for a leg prosthesis is disclosed by Martin et al. in U.S. Pat. No. 5,897,594. Unlike earlier solutions wherein the artificial foot has a rigid construction provided with a joint in order to imitate the function of the ankle, the jointless artificial foot of Martin et al. employs a resilient foot insert which is arranged inside a foot molding. The insert is of approximately C-shaped design in longitudinal section, with the opening to the rear, and takes up the prosthesis load with its upper C-limb and via its lower C-limb transmits that load to a leaf spring connected thereto. The leaf spring as seen from the underside is of convex design and extends approximately parallel to the sole region, forward beyond the foot insert into the foot-tip region. The Martin et al. invention is based on the object of improving the jointless artificial foot with regard to damping the impact of the heel, the elasticity, the heel-to-toe walking and the lateral stability, in order thus to permit the wearer to walk in a natural manner, the intention being to allow the wearer both to walk normally and also to carry out physical exercise and to play sports. However, the dynamic response characteristics of this known artificial foot are limited. There is a need for a higher performance prosthetic foot having improved applied mechanics design features which can improve amputee athletic performances involving activities such as running, jumping, sprinting, starting, stopping and cutting, for example.

Other prosthetic feet have been proposed by Van L. Phillips which allegedly provide an amputee with an agility and mobility to engage in a wide variety of activities which were precluded in the past because of the structural limitations and corresponding performances of prior art prostheses. Running, jumping and other activities are allegedly sustained by these known feet which, reportedly, may be utilized in the same manner as the normal foot of the wearer. See U.S. Pat. Nos. 6,071,313; 5,993,488; 5,899,944; 5,800,569; 5,800,568; 5,728,177; 5,728,176; 5,824,112; 5,593,457 5,514,185; 5,181,932; and 4,822,363, for example.

DISCLOSURE OF INVENTION

In order to allow the amputee athlete to attain a higher level of performance, there is a need for a high performance prosthetic foot having improved applied mechanics, which foot can out perform the human foot and also out perform the prior art prosthetic feet. It is of interest to the amputee athlete to have a high performance prosthetic foot having improved applied mechanics, high low dynamic response, and alignment adjustability that can be fine tuned to improve the horizontal and vertical components of activities which can be task specific in nature.

The prosthetic foot of the present invention addresses these needs. According to an example embodiment disclosed herein, the prosthetic foot of the invention comprises a longitudinally extending foot keel having a forefoot portion at one end, a hindfoot portion at an opposite end and a relatively long midfoot portion extending between and upwardly arched from the forefoot and hindfoot portions. A calf shank including a downward convexly curved lower end is also provided. An adjustable fastening arrangement attaches the curved lower end of the calf shank to the upwardly arched midfoot portion of the foot keel to form an ankle joint area of the prosthetic foot.

The adjustable fastening arrangement permits adjustment of the alignment of the calf shank and the foot keel with respect to one another in the longitudinal direction of the foot keel for tuning the performance of the prosthetic foot. By adjusting the alignment of the opposed upwardly arched midfoot portion of the foot keel and the downward convexly curved lower end of the calf shank with respect to one another in the longitudinal direction of the foot keel, the dynamic response characteristics and motion outcomes of the foot are changed to be task specific in relation to the needed/desired horizontal and vertical linear velocities. A multi-use prosthetic foot is disclosed having high and low dynamic response capabilities, as well as biplanar motion characteristics, which improve the functional outcomes of amputees participating in sporting and/or recreational activities. A prosthetic foot especially for sprinting is also disclosed.

The prosthetic foot can also include a device to limit the extent of the motion of the upper end of the calf shank in response to force loading and unloading the calf shank during use of the prosthetic foot. In one embodiment, the device is a piston-cylinder unit connected between the upper and lower ends of the calf shank and containing at least one pressurized fluid to limit the extent of motion and also dampen the energy being stored or released during calf shank compression and expansion.

These and other objects, features and advantages of the present invention become more apparent from a consideration of the following detailed description of disclosed example embodiments of the invention and the accompanying drawings.

BRIEF DESCRIPTION OF THE DRAWINGS

FIG. 1 is a schematic illustration representing the two adjacent radii of curvatures $R_1$ and $R_2$, one against the other, of a foot keel and calf shank of a prosthetic foot of the invention which creates a dynamic response capability and motion outcome of the foot in gait in the direction of arrow B which is perpendicular to the tangential line A connecting the two radii.

FIG. 2 is a view similar to FIG. 1 but showing the alignment of the two radii having been changed in the prosthetic foot according to the invention to increase the horizontal component and decrease the vertical component of the dynamic response capability and motion outcome of the foot in gait so that arrow $B_1$, perpendicular to tangential line $A_1$, is more horizontally directed than is the case depicted in FIG. 1.

FIG. 3 is a side view of a prosthetic foot according to an example embodiment of the invention with pylon adapter and pylon connected thereto for securing the foot to the lower leg of an amputee.

FIG. 4 is a front view of the prosthetic foot with pylon adapter and pylon of FIG. 3.

FIG. 5 is a top view of the embodiment of FIGS. 3 and 4.

BEST MODE FOR CARRYING OUT THE INVENTION

Figure 6:
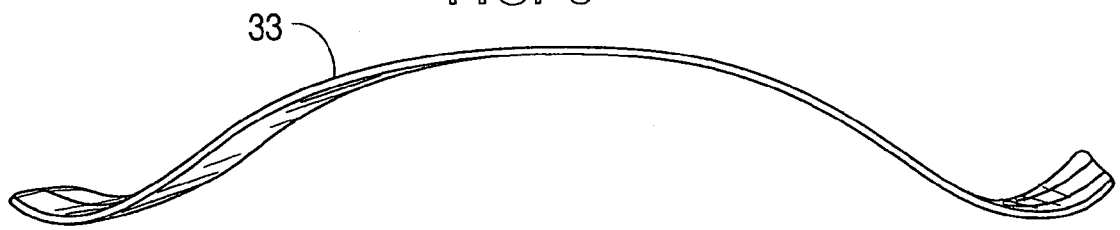
FIG. 6 is a side view of another foot keel of the invention, especially for sprinting, which may be used in the prosthetic foot of the invention.

Referring now to the drawings, a prosthetic foot 1 in the example embodiment of FIGS. 3-5 is seen to comprise a longitudinally extending foot keel 2 having a forefoot portion 3 at one end, a hindfoot portion 4 at an opposite end and an upwardly arched midfoot portion 5 extending between the forefoot and hindfoot portions. The midfoot portion 5 is upward convexly curved over its entire longitudinal extent between the forefoot and hindfoot portions in the example embodiment.

An upstanding calf shank 6 of the foot 1 attached at a portion of a downward convexly curved lower end 7 thereof to a proximate, posterior surface of the keel midfoot portion 5 by way of a releasable fastener 8 and coupling element/ankle coupler 11. The fastener 8 is a single bolt with nut and washers In the example embodiment, but could be a releasable clamp or other fastener for securely positioning and retaining the calf shank on the foot keel when the fastener is tightened.

Figure 8:
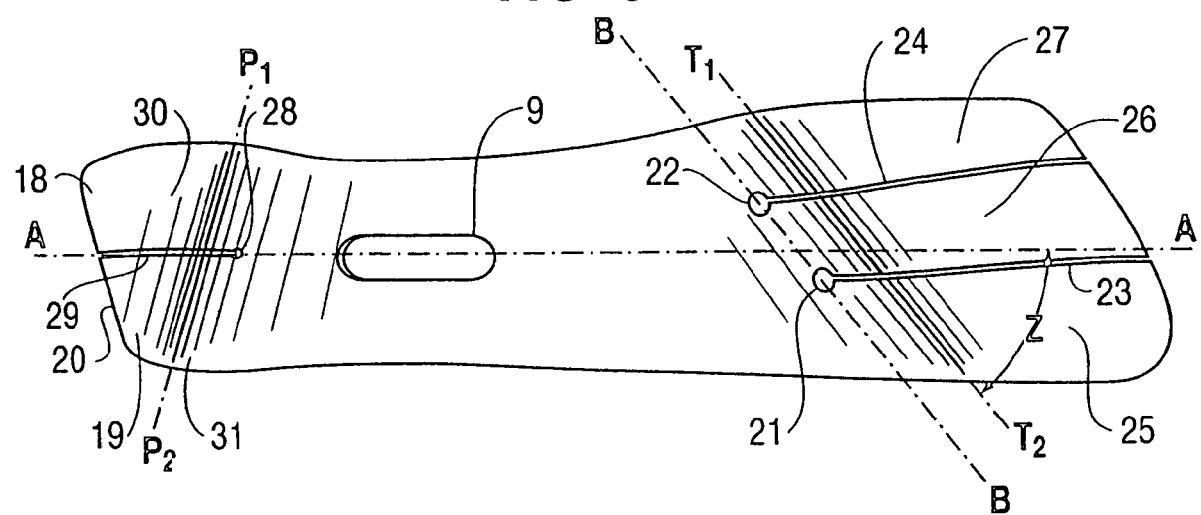
FIG. 8 is a bottom view of the foot keel in the prosthetic foot in FIG. 3 which provides high low dynamic response characteristics as well as biplanar motion capabilities.
Figure 15:
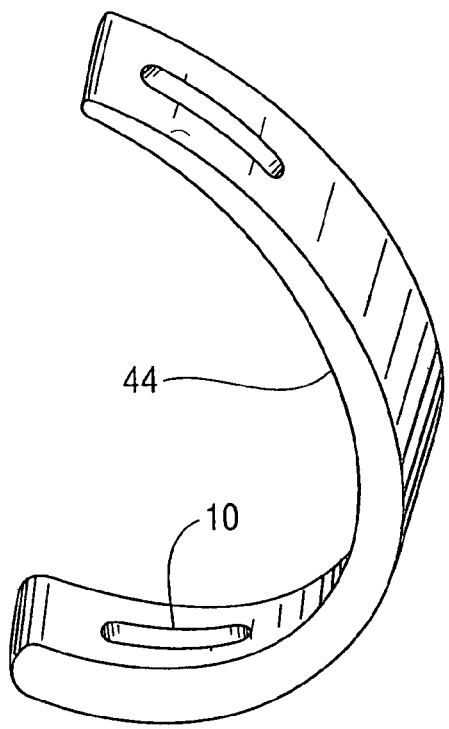
FIG. 15 is a side view from slightly above and to the front of a parabola shaped calf shank of the prosthetic foot of the invention, the thickness of the calf shank tapering toward its upper end.

A longitudinally extending opening 9 is formed in a proximate, posterior surface of the keel midfoot portion 5, see FIG. 8. A longitudinally extending opening 10 is also formed in the curved lower end 7 of the calf shank 6 like that shown in FIG. 15, for example. The releasable fastener 8 extends through the openings 9 and 10 which permit adjusting the alignment of the calf shank and the foot keel with respect to one another in the longitudinal direction, A-A in FIG. 5, when the fastener 8 is loosened or released for tuning the performance of the prosthetic foot to be task specific. Thus, the fastener 8, coupling element 11 and longitudinally extending openings 9 and 10 constitute an adjustable fastening arrangement for attaching the calf shank to the foot keel to form an ankle joint area of the prosthetic foot.

The effects of adjusting the alignment of the calf shank 6 and foot keel 2 are seen from a consideration of FIGS. 1 and 2, wherein the two radii $R_1$ and $R_2$, one next to another, represent the adjacent, facing, domed or convexly curved surfaces of the foot keel midportion 5 and the calf shank 6. When two such radii are considered one next to another, motion capability exists perpendicular to a tangential line, A in FIG. 1, $A_1$ in FIG. 2, drawn between the two radii. The interrelationship between these two radii determines a direction of motion outcomes. As a consequence, dynamic response force application of the foot 1 is dependent on this relationship. The larger the radius of a concavity, the more dynamic response capability. However, the tighter a radius, the quicker it responds.

The alignment capability of the calf shank and foot keel in the prosthetic foot of the invention allows the radii to be shifted so that horizontal or vertical linear velocities with the foot in athletic activities are affected. For example, to improve the horizontal linear velocity capability of the prosthetic foot 1, an alignment change can be made to affect the relationship of the calf shank's radius and the foot keel radius. That is, to improve the horizontal linear velocity characteristic, the bottom radius $R_2$, of the foot keel, is made more distal than its start position, FIG. 2 as compared with FIG. 1. This changes the dynamic response characteristics and motion outcomes of the foot 1 to be more horizontally directed and as a result greater horizontal linear velocity can be achieved with the same applied forces.

Figure 23:
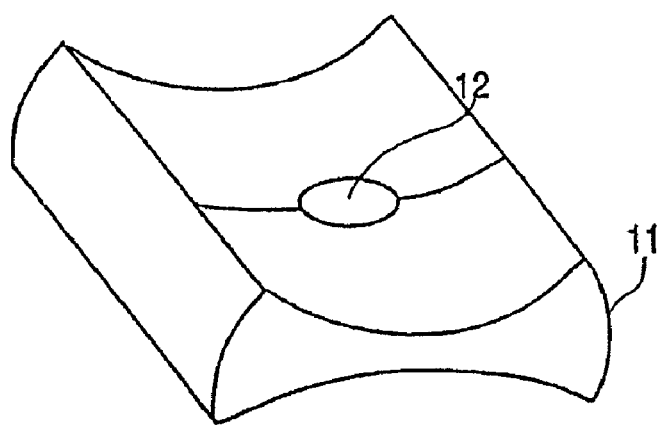
FIG. 23 is a side view, from slightly above, of a metal alloy or plastic coupling element used in the adjustable fastening arrangement of the invention for attaching the calf shank to the foot keel as shown in FIG. 3.
Figure 24:
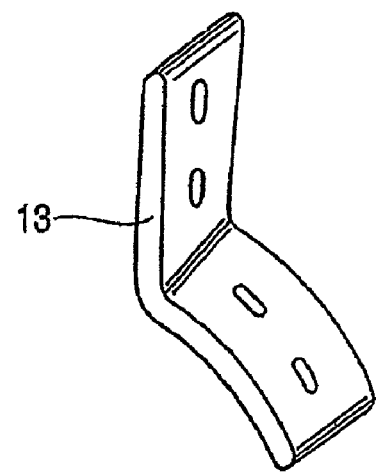
FIG. 24 is a view from the side and slightly to the front of a pylon adapter used on the prosthetic foot of FIGS. 3-5, and also useful with the foot of FIGS. 28 and 29, for connecting the foot to a pylon to be attached to an amputee's leg.

The amputee can, through practice, find a setting for each activity that meets his/her needs as these needs relate to horizontal and vertical linear velocities. A jumper and a basketball player, for example, need more vertical lift than a sprint runner. The coupling element 11 is a plastic or metal alloy alignment coupling (see FIGS. 3, 4 and 23) sandwiched between the attached foot keel 2 and calf shank 6. The releasable fastener 8 extends through a hole 12 in the coupling element. The coupling element extends along the attached portion of the calf shank and the proximate, posterior surface of the keel midfoot portion 5.

The curved lower end 7 of the calf shank 6 is in the shape of a parabola with the smallest radius of curvature of the parabola located at the lower end and extending upwardly, and initially anteriorly in the parabola shape. A posteriorly facing concavity is formed by the curvature of the calf shank as depicted in FIG. 3. The parabola shape is advantageous in that it has increased dynamic response characteristics in creating both improved horizontal linear velocity associated with the relatively larger radii proximal terminal end thereof, while having a smaller radius of curvature at its lower end for quicker response characteristics. The larger radii of curvature at the upper end of the parabola shape enable the tangential line A, explained with reference to FIGS. 1 and 2, to remain more vertically oriented with changes in alignment, which creates improved horizontal linear velocity.

The parabolic shaped calf shank responds to initial contact ground forces in human gait by compressing or coiling in on itself. This makes the radii of the parabola curve smaller, and as a consequence, the resistance to compression is decreased. In contrast, as the parabolic shaped calf shank responds to heel off ground reaction forces (GRFs) in human gait by expanding, this makes the radii of the parabola curve larger and as a consequence resistance is much greater than the aforementioned compressive resistance. These resistances are associated with the human's anterior and posterior calf muscle function in human gait. At initial contact to foot flat of human gait, the smaller anterior calf muscle group responds to GRFs by eccentrically contracting to lower the foot to the ground and a dorsiflexion moment is created. From foot flat to toe off the larger posterior calf muscle group responds to GRFs also by eccentrically contracting and a greater plantar flexion moment is created. This moment size relates to the calf anterior and posterior muscle group difference in size. As a consequence, the prosthetic calf shank's resistance to the dorsiflexion and plantar flexion moments in human gait are mimicked and normal gait is achieved. The parabolic curves variable resistance capability mimics the human calf musculature function in human gait and running and jumping activities, and as a consequence prosthetic efficiency is achieved.

A human being walks at approximately three miles per hour. A 4:00 minute miler runs at 12 miles per hour and a 10 second, 100 meter sprinter sprints at 21 miles per hour. This is a 1 to 4 to 7 ratio. The horizontal component of each task is greater as the velocity of the activity increases. As a consequence, the size of the prosthetic calf shank radii can be predetermined. A walker needs a smaller radii parabolic curved calf shank than a miler and a sprinter. A sprint runner needs a parabolic curved calf shank that is seven times as large. This relationship shows how to determine the parabolic radii for walkers, runners and sprinters. It is of significance because sprint runners have increased range of motion requirements and their calf shanks must be stronger to accept the increased loads associated with this activity. A wider or larger parabolic calf shank will be a relatively flatter curve, which equates to greater structural strength with increased range of motion.

A pylon adapter 13 is connected to the upper end of the calf shank 6 by fasteners 14. The adapter 13 in turn is secured to the lower end of pylon 15 by fasteners 16. Pylon 15 is secured to the lower limb of the amputee by a supporting structure (not shown) attached to the leg stump.

The forefoot, midfoot and hindfoot portions of the foot keel 2 are formed of a single piece of resilient material in the example embodiment. For example, a solid piece of material, plastic in nature, having shape-retaining characteristics when deflected by the ground reaction forces can be employed. More particularly, the foot keel and also the calf shank can be formed of laminated composite material having reinforcing fiber laminated with polymer matrix material. In particular, a high strength graphite, laminated with epoxy thermosetting resins, or extruded plastic utilized under the tradename of Delran, or degassed polyurethane copolymers, may be used to form the foot keel and also the calf shank. The functional qualities associated with these materials afford high strength with low weight and minimal creep. The thermosetting epoxy resins are laminated under vacuum utilizing prosthetic industry standards. The polyurethane copolymers can be poured into negative molds and the extruded plastic can be machined. Each material of use has its advantages and disadvantages. It has been found that the laminated composite material for the foot keel and the calf shank can also advantageously be a thermo-formed (prepreg) laminated composite material manufactured per industry standards, with reinforcing fiber and a thermoplastic polymer matrix material for superior mechanical expansion qualities. A suitable commercially available composite material of this kind is CYLON® made by Cytec Fiberite Inc. of Havre de Grace, Md.

The resilient material's physical properties as they relate to stiffness, flexibility and strength are all determined by the thickness of the material. A thinner material will deflect easier than a thicker material of the same density. The material utilized, as well as the physical properties, are associated with the stiffness to flexibility characteristics in the prosthetic foot keel and calf shank. The thickness of the foot keel and calf shank are uniform or symmetrical in the example embodiment of FIGS. 3-5, but the thickness along the length of these components can be varied as discussed below, such as by making the hindfoot and forefoot areas thinner and more responsive to deflection in the midfoot region.

To aid in providing the prosthetic foot 1 with a high low dynamic response capability, the midfoot portion 5 is formed by a longitudinal arch such that the medial aspect of the longitudinal arch has a relatively higher dynamic response capability than the lateral aspect of the longitudinal arch. For this purpose, in the example embodiment, the medial aspect of the longitudinal arch concavity is larger in radius than the lateral aspect thereof.

The interrelationship between the medial to lateral radii size of the longitudinal arch concavity of the midfoot portion 5 is further defined as the anterior posterior plantar surface weight bearing surface areas of the foot keel 2. The line $T_1$-$T_2$ on the anterior section of 5 in FIG. 8 represents the anterior plantar surface weight bearing area. Line $P_1$-$P_2$ represents the posterior plantar weight-bearing surface of 5. The plantar weight bearing surfaces on the lateral side of the foot would be represented by the distance between $T_1$-$P_1$. The plantar weight bearing surfaces on the medial side of the foot 2 are represented by the distance between $P_2$-$T_2$. The distances represented by $T_1$-$P_1$ and $P_2$-$T_2$ determine the radii size, and as a result the high low dynamic response interrelationship is determined and can be influenced by converging or diverging these two lines $T_1$-$T_2$ to $P_1$-$P_2$. As a result, high low dynamic response can be determined in structural design.

The posterior end 17 of the hindfoot portion 4 is shaped in an upwardly curved arch that reacts to ground reaction forces during heel strike by compressing for shock absorption. The heel formed by the hindfoot portion 4 is formed with a posterior lateral corner 18 which is more posterior and lateral than the medial corner 19 to encourage hindfoot eversion during initial contact phase of gait. The anterior end 20 of the forefoot portion 3 is shaped in an upwardly curved arch to simulate the human toes being dorsiflexed in the heel rise toe off position of the late stance phase of gait. Rubber or foam pads 53 and 54 are provided on the lower forefoot and hindfoot as cushions.

Improved biplanar motion capability of the prosthetic foot is created by medial and lateral expansion joint holes 21 and 22 extending through the forefoot portion 3 between dorsal and plantar surfaces thereof. Expansion joints 23 and 24 extend forward from respect ones of the holes to the anterior edge of the forefoot portion to form medial, middle and lateral expansion struts 25-27 which create improved biplanar motion capability of the forefoot portion of the foot keel. The expansion joint holes 21 and 22 are located along a line, B-B in FIG. 5, in the transverse plane which extends at an angle α of 35° to the longitudinal axis A-A of the foot keel with the medial expansion joint hole 21 more anterior than the lateral expansion joint hole 22.

The angle α of line B-B to longitudinal axis A-A in FIG. 5 can be as small as 15° and still derive a high low dynamic response. As this angle α changes, so should the angle Z of the line $T_1$-$T_2$ in FIG. 8. The expansion joint holes 21 and 22 as projected on a sagittal plane are inclined at an angle of 45° to the transverse plane with the dorsal aspect of the holes being more anterior than the plantar aspect. With this arrangement, the distance from the releasable fastener 8 to the lateral expansion joint hole 22 is shorter than the distance from the releasable fastener to the medial expansion joint hole 21 such that the lateral portion of the prosthetic foot 1 has a shorter toe lever than the medial for enabling midfoot high and low dynamic response. In addition, the distance from the releasable fastener 8 to the lateral plantar weight bearing surface as represented by $T_1$, line is shorter than the distance from the releasable fastener to the medial plantar surface weight bearing surface as represented by the line $T_2$—such that the lateral portion of the prosthetic foot 1 has a shorter toe lever than the medial for enabling midfoot high low dynamic response.

The anterior of the hindfoot portion 4 of the foot keel 2 further includes an expansion joint hole 28 extending through the hindfoot portion 4 between dorsal and plantar surfaces thereof. An expansion joint 29 extends posteriorly from the hole 28 to the posterior edge of the hindfoot portion to form expansion struts 30 and 31. These create improved biplanar motion capability of the hindfoot portion of the foot.

A dorsal aspect of the midfoot portion 5 and the forefoot portion 3 of the foot keel 2 form the upwardly facing concavity, 32 in FIG. 3, so that it mimics in function the fifth ray axis of motion of a human foot. That is, the concavity 32 has a longitudinal axis C-C which is oriented at an angle β of 15° to 35° to the longitudinal axis A-A of the foot keel with the medial being more anterior than the lateral to encourage fifth ray motion in gait as in the oblique low gear axis of rotation of the second to fifth metatarsals in the human foot.

The importance of biplanar motion capability can be appreciated when an amputee walks on uneven terrain or when the athlete cuts medially or laterally on the foot. The direction of the ground force vector changes from being sagittally oriented to having a frontal plane component. The ground will push medially in opposite direction to the foot pushing laterally. As a consequence to this, the calf shank leans medially and weight is applied to the medial structure of the foot keel. In response to these pressures, the medial expansion joint struts 25 and 31 of the foot keel 2 dorsiflex (deflect upward) and invert, and the lateral expansion joint struts 27 and 30 plantar flex (deflect downwards) and evert. This motion tries to put the plantar surface of the foot flat on the ground (plantar grade).

Figure 7:
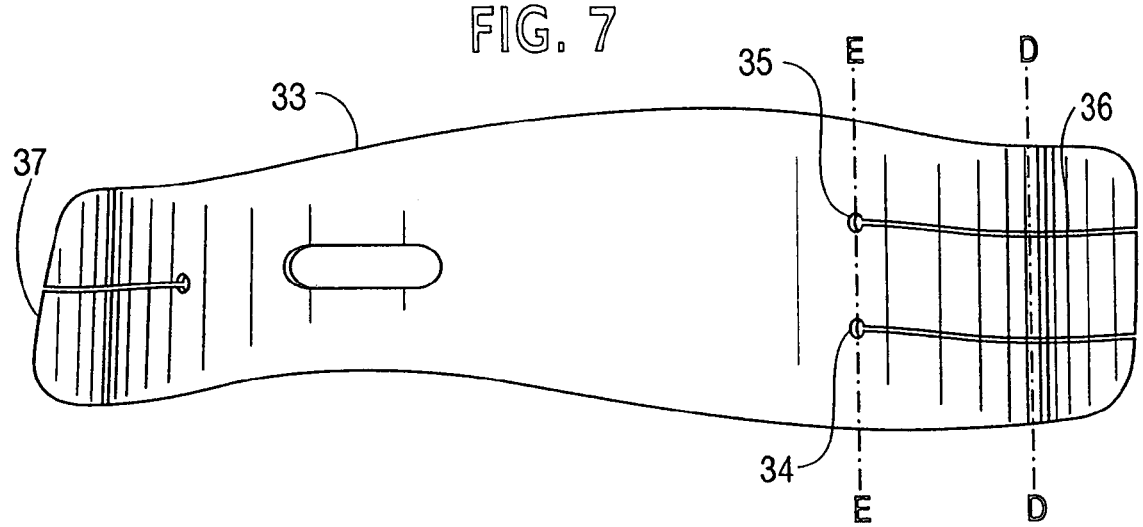
FIG. 7 is a top view of the foot keel of FIG. 6.

Another foot keel 33 of the invention, especially for sprinting, may be used in the prosthetic foot of the invention, see FIGS. 6 and 7. The body's center of gravity in a sprint becomes almost exclusively sagittal plane oriented. The prosthetic foot does not need to have a low dynamic response characteristic. As a consequence, the 15° to 35° external rotation orientation of the longitudinal axis of the forefoot, midfoot concavity as in foot keel 2 is not needed. Rather, the concavity's longitudinal axis D-D orientation should become parallel to the frontal plane as depicted in FIGS. 6 and 7. This makes the sprint foot respond in a sagittal direction only. Further, the orientation of the expansion joint holes 34 and 35 in the forefoot and midfoot portions, along line E-E, is parallel to the frontal plane, i.e., the lateral hole 35 is moved anteriorly and in line with the medial hole 34 and parallel to the frontal plane. The anterior terminal end 36 of the foot keel 33 is also made parallel to the frontal plane. The posterior terminal heel area 37 of the foot keel is also parallel to the frontal plane. These modifications effect in a negative way the multi-use capabilities of the prosthetic foot. However, its performance characteristics become task specific. Another variation in the sprint foot keel 33 is in the toe, ray region of the forefoot portion of the foot where 15° of dorsiflexion in the foot keel 2 are increased to 25-40° of dorsiflexion in foot keel 33.

Figure 9:
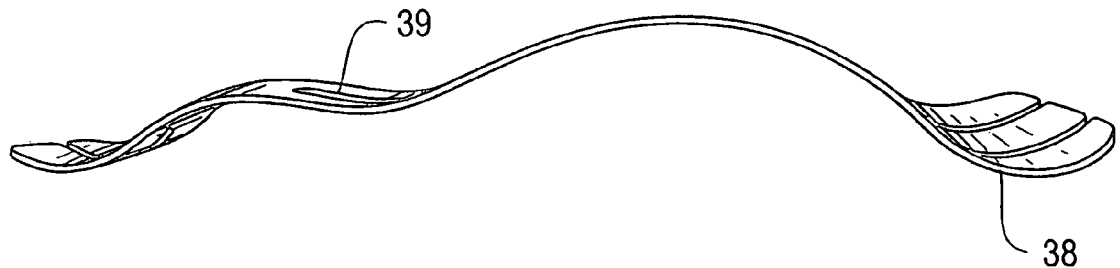
FIG. 9 is a side view of an additional foot keel of the invention for the prosthetic foot particularly useful for sprinting by an amputee that has had a Symes amputation of the foot.
Figure 10:
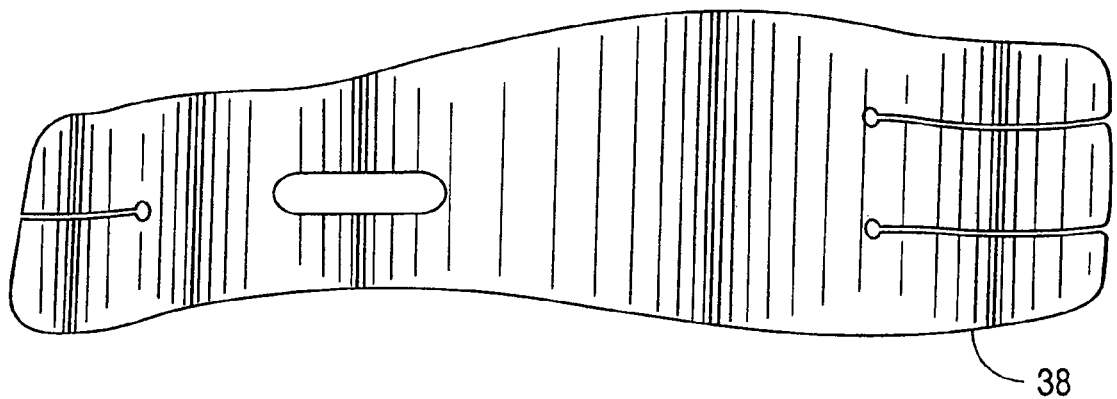
FIG. 10 is a top view of the foot keel of FIG. 9.
Figure 11:
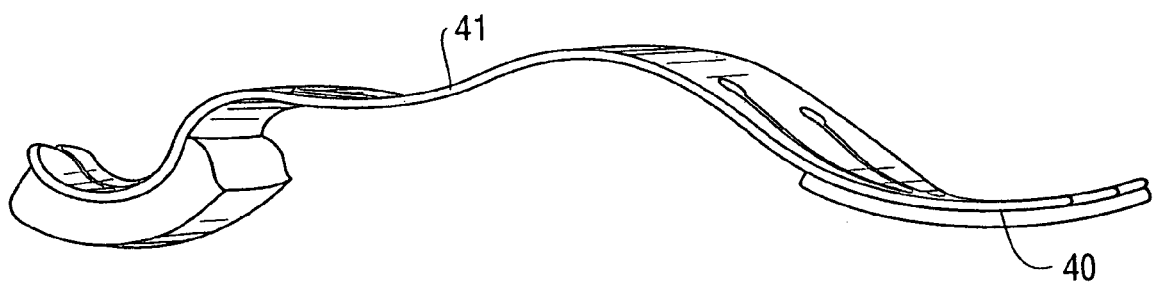
FIG. 11 is a further variation of foot keel for the prosthetic foot of the invention for a Symes amputee, the foot keel providing the prosthetic foot with high low dynamic response characteristics as well as biplanar motion capabilities.
Figure 12:
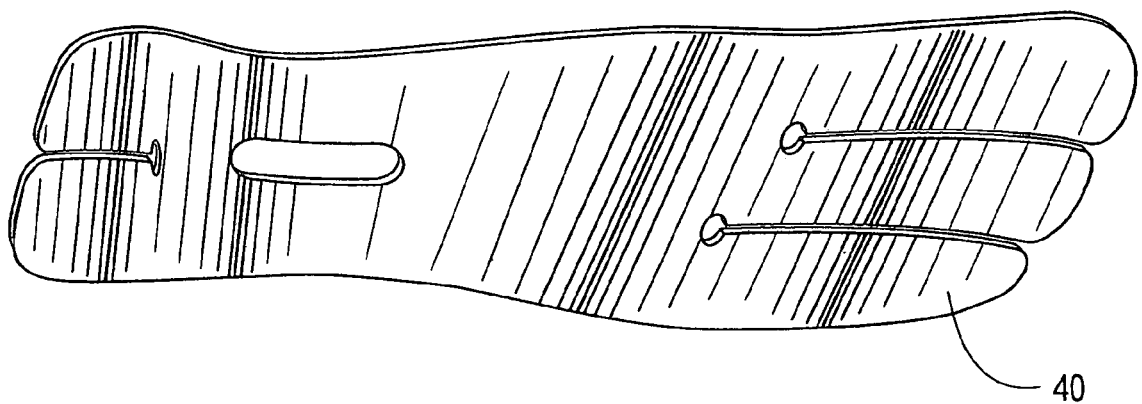
FIG. 12 is a top view of the foot keel of FIG. 11.

FIGS. 9 and 10 show an additional foot keel 38 of the invention for the prosthetic foot particularly useful for sprinting by an amputee that has had a Symes amputation of the foot. For this purpose, the midfoot portion of the foot keel 38 includes a posterior, upwardly facing concavity 39 in which the curved lower end of the calf shank is attached to the foot keel by way of the releasable fastener. This foot keel can be utilized by all lower extremity amputees. The foot keel 38 accommodates the longer residual limb associated with the Symes level amputee. Its performance characteristics are distinctively quicker in dynamic response capabilities. Its use is not specific to this level of amputation. It can be utilized on all transtibial and transfemoral amputations. The foot keel 40 in the example embodiment of FIGS. 11 and 12 also has a concavity 41 for a Symes amputee, the foot keel providing the prosthetic foot with high low dynamic response characteristic as well as biplanar motion capabilities like those of the example embodiment in FIGS. 3-5 and 8.

The functional characteristics of the several foot keels for the prosthetic foot 1 are associated with the shape and design features as they relate to concavities, convexities, radii size, expansion, compression, and material physical properties—all of these properties relating, to reacting to, ground forces in walking, running and jumping activities.

Figure 13:
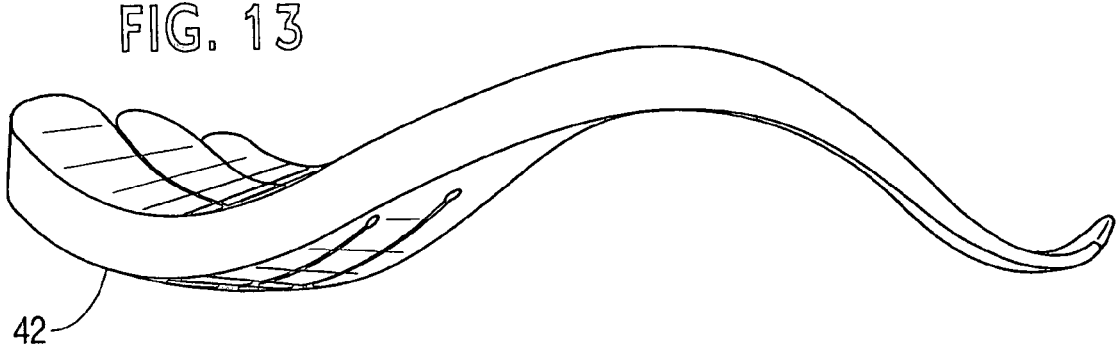
FIG. 13 is a side view of a foot keel of the invention wherein the thickness of the keel tapers, e.g., is progressively reduced, from the midfoot portion to the hindfoot portion of the keel.
Figure 14:
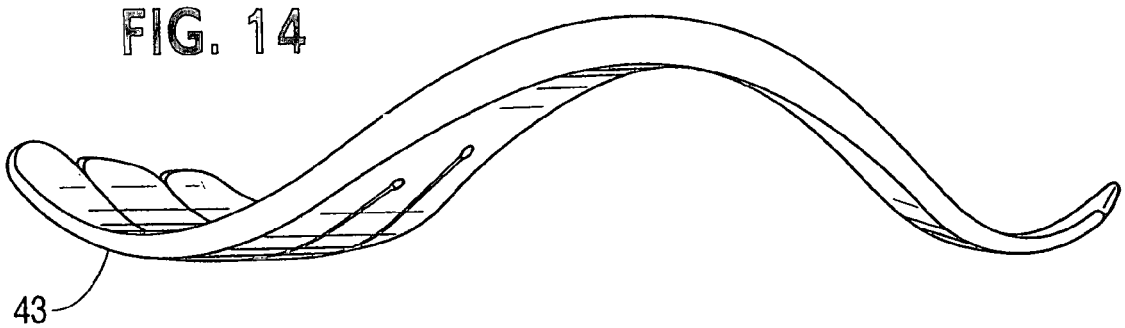
FIG. 14 is a side view of another form of the foot keel wherein the thickness tapers from the midfoot toward both the forefoot and hindfoot of the keel.
Figure 16:
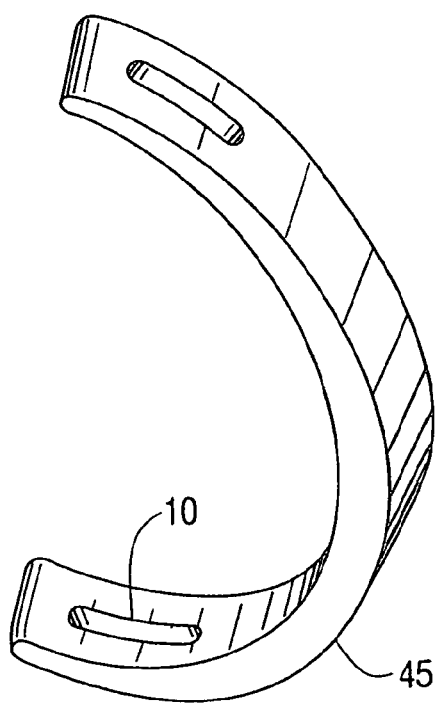
FIG. 16 is a side view like FIG. 15 but showing another calf shank tapered from the middle towards both its upper and lower ends.
Figure 17:
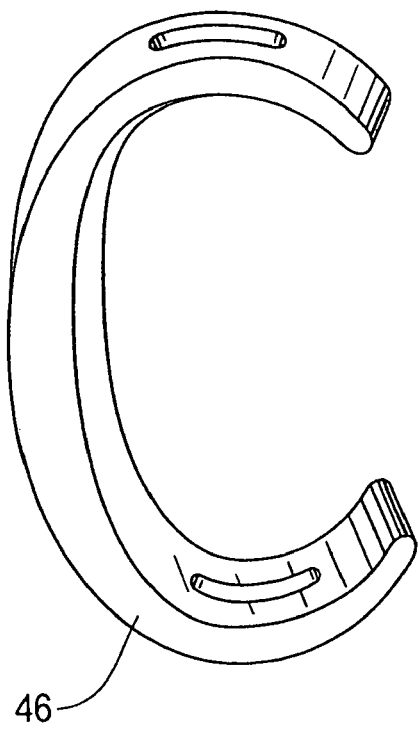
FIG. 17 is a side view of a C-shaped calf shank for the prosthetic foot, the calf shank thickness tapering from the middle towards both its upper and lower ends.
Figure 18:
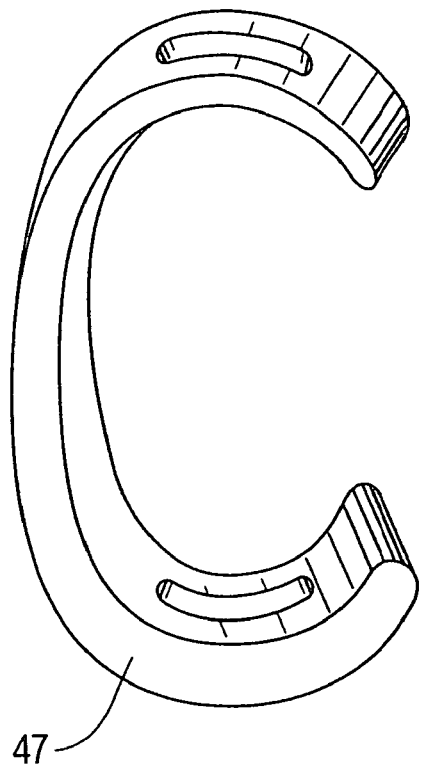
FIG. 18, is a side view of another example of a C-shaped calf shank for the prosthetic foot, the thickness of the calf shank being progressively reduced from its midportion to its upper end.
Figure 19:
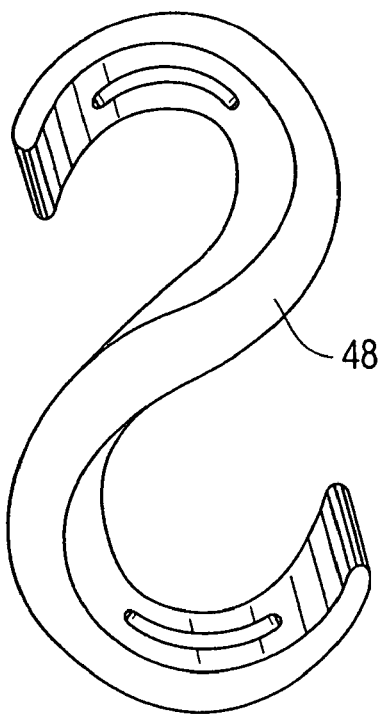
FIG. 19 is a side view of an S-shaped calf shank for the prosthetic foot, both ends being progressively reduced in thickness from the middle thereof.
Figure 20:
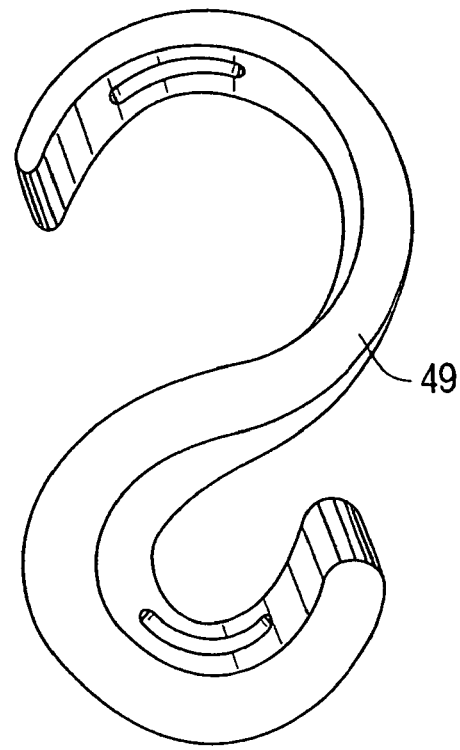
FIG. 20 is a further example of an S-shaped calf shank which is tapered in thickness only at its upper end.
Figure 21:
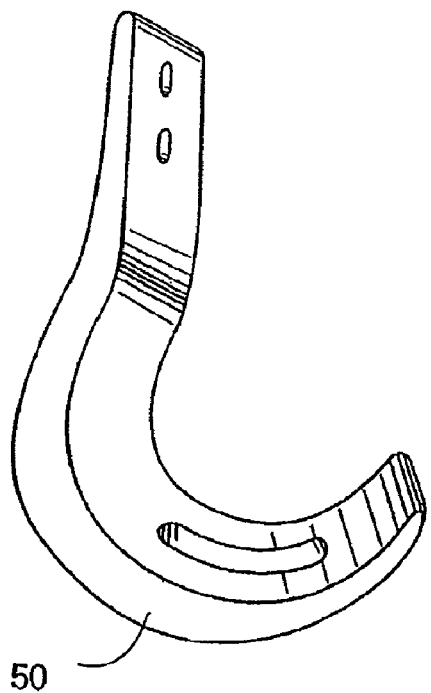
FIG. 21 is a side view of a J-shaped calf shank, tapered at each end, for the prosthetic foot of the invention.
Figure 22:
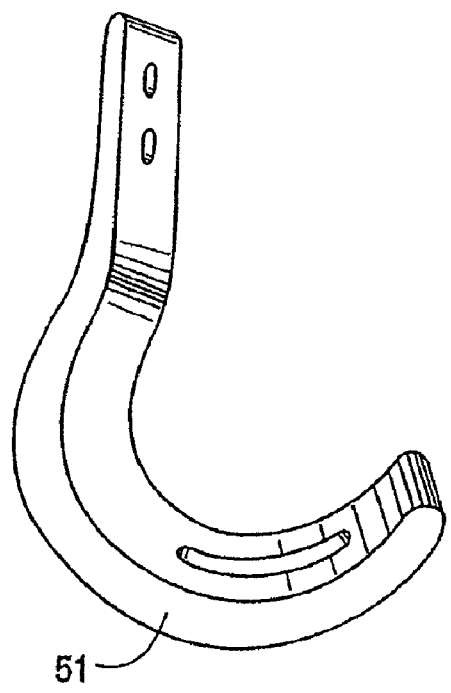
FIG. 22 is a view like FIG. 21 but showing a J-shaped calf shank which is progressively reduced in thickness towards only its upper end.

The foot keel 42 in FIG. 13 is like that in the example embodiment of FIGS. 3-5 and 8, except that the thickness of the foot keel is tapered from the midfoot portion to the posterior of the hindfoot. The foot keel 43 in FIG. 14 has its thickness progressively reduced or tapered at both its anterior and posterior ends. Similar variations in thickness are shown in the calf shank 44 of FIG. 15 and the calf shank 45 of FIG. 16 which may be used in the prosthetic foot 1. Each design of the foot keel and calf shank create different functional outcomes, as these function outcomes relate to the horizontal and vertical linear velocities which are specific to improving performance in varied athletic related tasks. The capability of multiple calf shank configurations and adjustments in settings between the foot keel and the calf shank create a prosthetic foot calf shank relationship that allows the amputee and/or the prosthetist the ability to tune the prosthetic foot for maximum performance in a selected one of a wide variety of sport and recreational activities.

Other calf shanks for the prosthetic foot 1 are illustrated in FIGS. 17-22 and include C-shaped calf shanks 46 and 47, S-shaped calf shanks 48 and 49 and J-shaped calf shanks 50 and 51. The upper end of the calf shank could also have a straight vertical end with a pyramid attachment plate attached to this proximal terminal end. A male pyramid could be bolted to and through this vertical end of the calf shank. Plastic or aluminum fillers to accept the proximal male pyramid and the distal foot keel could also be provided in the elongated openings at the proximal and distal ends of the calf shank. The prosthetic foot of the invention is a modular system preferably constructed with standardized units or dimensions for flexibility and variety in use.

All track related running activities take place in a counter-clockwise direction. Another, optional feature of the invention takes into account the forces acting on the foot advanced along such a curved path. Centripetal acceleration acts toward the center of rotation where an object moves along a curved path. Newton's third law is applied for energy action. There is an equal and opposite reaction. Thus, for every "center seeking" force, there is a "center fleeing" force. The centripetal force acts toward the center of rotation and the centrifugal force, the reaction force, acts away from the center of rotation. If an athlete is running around the curve on the track, the centripetal force pulls the runner toward the center of the curve while the centrifugal force pulls away from the center of the curve. To counteract the centrifugal force which tries to lean the runner outward, the runner leans inward. If the direction of rotation of the runner on the track is always counter-clockwise, then the left side is the inside of the track. As a consequence, according to a feature of the present invention, the left side of the right and left prosthetic foot calf shanks can be made thinner than the right side and the amputee runner's curve performance could be improved.

The foot keels 2, 33, 38, 42 and 43 in the several embodiments, are each 29 cm long with the proportions of the shoe 1 shown to scale in FIGS. 3, 4 and 5, and in the several views of the different calf shanks and foot keels. However, as will be readily understood by the skilled artisan, the specific dimensions of the prosthetic foot can be varied depending on the size, weight and other characteristics of the amputee being fitted with the foot.

The operation of the prosthetic foot 1 in walking and running stance phase gait cycles will now be considered. Newton's three laws of motion, that relate to law of inertia, acceleration and action-reaction, are the basis for movement kinematics in the foot 2. From Newton's third law, the law of action-reaction, it is known that the ground pushes on the foot in a direction equal and opposite to the direction the foot pushes on the ground. These are known as ground reaction forces. Many scientific studies have been done on human gait, running and jumping activities. Force plate studies show us that Newton's third law occurs in gait. From these studies, we know the direction the ground pushes on the foot.

The stance phase of walking/running activities can be further broken down into deceleration and acceleration phases. When the prosthetic foot touches the ground, the foot pushes anteriorly on the ground and the ground pushes back in an equal and opposite direction—that is to say the ground pushes posteriorly on the prosthetic foot. This force makes the prosthetic foot move. The stance phase analysis of walking and running activities begins with the contact point being the posterior lateral corner 18, FIGS. 5 and 8, which is offset more posteriorly and laterally than the medial side of the foot. This offset at initial contact causes the foot to evert and the calf shank to plantar flex. The calf shank always seeks a position that transfers the body weight through its shank, e.g., it tends to have its long vertical member in a position to oppose the ground forces. This is why it moves posteriorly-plantar flexes to oppose the ground reaction force which is pushing posteriorly on the foot.

The ground forces cause calf shanks 44, 45, 46, 47, 50 and 51 to compress with the proximal end moving posterior. With calf shanks 48, 49 the distal ½ of the calf shank would compress depending on the distal concavities orientation. If the distal concavity compressed in response to the GRF's the proximal concavity would expand and the entire calf shank unit would move posteriorally. The ground forces cause the calf shank to compress with the proximal end moving posteriorly. The calf shank lower tight radius compresses simulating human ankle joint plantar flexion and the forefoot is lowered by compression to the ground. At the same time to the posterior aspect of keel, as represented by hindfoot 4, depicted by 17 compresses upward through compression. Both of these compressive forces act as shock absorbers. This shock absorption is further enhanced by the offset posterior lateral heel 18 which causes the foot to evert, which also acts as a shock absorber, once the calf shank has stopped moving into plantar flexion and with the ground pushing posteriorly on the foot.

The compressed members of the foot keel and calf shank then start to unload—that is they seek their original shape and the stored energy is released—which causes the calf shank proximal end to move anteriorly in an accelerated manner. As the calf shank approaches its vertical starting position, the ground forces change from pushing posteriorly to pushing vertically upward against the foot. Since the prosthetic foot has posterior and anterior plantar surface weight bearing areas and these areas are connected by a non-weight bearing long arch shaped midportion, the vertically directed forces from the prosthesis cause the long arch shaped midportion to load by expansion. The posterior and anterior weight-bearing surfaces diverge. These vertically directed forces are being stored in the long arch midportion of the foot—as the ground forces move from being vertical in nature to anteriorly directed. The calf shank expands—simulating ankle dorsiflexion. This causes the prosthetic foot to pivot off of the anterior plantar weight-bearing surface. As weight unloading occurs, the long arch of the midfoot portion 5 changes from being expanded and it seeks its original shape which creates a simulated plantar flexor muscle group burst. This releases the stored vertical compressed force energy into improved expansion capabilities.

The long arch of the foot keel and the calf shank resist expansion of their respective structures. As a consequence, the calf shank anterior progression is arrested and the foot starts to pivot off the anterior plantar surface weight-bearing area. The expansion of the midfoot portion of the foot keel has as high and low response capability in the case of the foot keels in the example embodiments of FIGS. 3-5 and 8, FIGS. 11 and 12, FIG. 13 and FIG. 14. Since the midfoot forefoot transitional area of these foot keels is deviated 15° to 35° externally from the long axis of the foot, the medial long arch is longer than the lateral long arch. This is important because in the normal foot, during acceleration or deceleration, the medial aspect of the foot is used.

The prosthetic foot longer medial arch has greater dynamic response characteristic than the lateral. The lateral shorter toe lever is utilized when walking or running at slower speeds. The body's center of gravity moves through space in a sinusoidal curve. It moves medial, lateral, proximal and distal. When walking or running at slower speeds, the body's center of gravity moves more medial and lateral than when walking or running fast. In addition, momentum or inertia is less and the ability to overcome a higher dynamic response capability is less. The prosthetic foot of the invention is adapted to accommodate these principles in applied mechanics.

In addition, in the human gait cycle at midstance the body's center of gravity is as far lateral as it will go. From midstance through toe off the body's center of gravity (BCG) moves from lateral to medial. As a consequence, the body's center of gravity progresses over the lateral side of the foot keel 2. First (low gear) and as the BCG progresses forward, it moves medially on foot keel 2 (high gear). As a consequence, the prosthetic foot keel 2 has an automatic transmission effect. That is to say, it starts in low gear and moves into high gear every step the amputee takes.

As the ground forces push anteriorly on the prosthetic foot which is pushing posteriorly on the ground, as the heel begins to rise the anterior portion of the long arch of the midfoot portion is contoured to apply these posteriorly directed forces perpendicular to its plantar surface. This is the most effective and efficient way to apply these forces. The same can be said about the posterior hindfoot portion of the prosthetic foot. It is also shaped so that the posteriorly directed ground forces at initial contact are opposed with the foot keel's plantar surface being perpendicular to their applied force direction.

In the later stages of heel rise, toe off walking and running activities, the ray region of the forefoot portion is dorsiflexed 15°-35°. This upwardly extending arc allows the anteriorly directed ground forces to compress this region of the foot. This compression is less resisted than expansion and a smooth transition occurs to the swing phase of gait and running with the prosthetic foot. In later stages of stance phase of gait, the expanded calf shank and the expanded midfoot long arch release their stored energy adding to the propulsion of the amputee's body center of gravity.

One of the main propulsion mechanisms in human gait is called the active propulsion phase. As the heel lifts, the body weight is now forward of the support limb and the center of gravity is falling. As the body weight drops over the forefoot rocker FIG. 5, line C-C there is a downward acceleration, which results in the highest vertical force received by the body. Acceleration of the leg forward of the ankle, associated with lifting of the heel, results in a posterior shear against the ground. As the center of pressure moves anterior to the metatarsal heads axis of rotation the effect is an ever-increasing dorsiflexion torque. This creates a full forward fall situation that generates the major progression force used in walking. The signs of effective ankle function during the active propulsion are heel lift, minimal joint motion, and a nearly neutral ankle position. A stable midfoot is essential for normal sequencing in heel lift.

The posterior aspect of the hindfoot and the forefoot region of the foot keel incorporate expansion joint holes and expansion joint struts in several of the embodiments as noted previously. The orientation of the expansion joint holes act as a mitered hinge and biplanar motion capabilities are improved for improving the total contact characteristics of the plantar surface of the foot when walking on uneven terrain.

The Symes foot keels in FIGS. 9-12 are distinctively different in dynamic response capabilities—as these capabilities are associated with walking, running and jumping activities. These foot keels differ in four distinct features. These include the presence of a concavity in the proximate, posterior of the midfoot portion for accommodating the Symes distal residual limb shape better than a flat surface. This concavity also lowers the height of the foot keel which accommodates the longer residual limb that is associated with the Symes level amputee. The alignment concavity requires that the corresponding anterior and posterior radii of the arched foot keel midportion be more aggressive and smaller in size. As a consequence, all of the midfoot long arch radii and the hindfoot radii are tighter and smaller. This significantly affects the dynamic response characteristics. The smaller radii create less potential for a dynamic response. However, the prosthetic foot responds quicker to all of the aforementioned walking, running and jumping ground forces. The result is a quicker foot with less dynamic response.

Improved task specific athletic performance can be achieved with alignment changes using the prosthetic foot of the invention, as these alignment changes affect the vertical and horizontal components of each task. The human foot is a multi-functional unit—it walks, runs and jumps. The human tibia fibula calf shank structure on the other hand is not a multi-functional unit. It is a simple lever which applies its forces in walking, running and jumping activities parallel to its long proximal-distal orientation. It is a non-compressible structure and it has no potential to store energy. On the other hand, the prosthetic foot of the invention has dynamic response capabilities, as these dynamic response capabilities are associated with the horizontal and vertical linear velocity components of athletic walking, running and jumping activities and out-performing the human tibia and fibula. As a consequence, the possibility exists to improve amputee athletic performance. For this purpose, according to the present invention, the fastener 8 is loosened and the alignment of the calf shank and the foot keel with respect to one another is adjusted in the longitudinal direction of the foot keel. Such a change is shown in connection with FIGS. 1 and 2. The calf shank is then secured to the foot keel in the adjusted position with the fastener 8. During this adjustment, the bolt of the fastener 8 slides relative to one or both of the opposed, relatively longer, longitudinally extending openings 9 and 10 in the foot keel and calf shank, respectively.

An alignment change that improves the performance characteristic of a runner who makes initial contact with the ground with the foot flat as in a midfoot strike runner, for example, is one wherein the foot keel is slid anterior relative to the calf shank and the foot plantar flexed on the calf shank. This new relationship improves the horizontal component of running. That is, with the calf shank plantar flexed to the foot, and the foot making contact with the ground in a foot flat position as opposed to initially heel contact, the ground immediately pushes posteriorly on the foot that is pushing anteriorly on the ground. This causes the calf shank to move rapidly forward (by expanding) and downwardly. Dynamic response forces are created by expansion which resists the calf shank's direction of initial movement. As a consequence, the foot pivots over the metatarsal plantar surface weight-bearing area. This causes the midfoot region of the keel to expand which is resisted more than compression. The net effect of the calf shank expansion and the midfoot expansion is that further anterior progression of the calf shank is resisted which allows the knee extenders and hip extenders in the user's body to move the body's center of gravity forward and proximal in a more efficient manner (i.e., improved horizontal velocity). In this case, more forward than up than in the case of a heel toe runner whose calf shank's forward progression is less resisted by the calf shank starting more dorsiflexed (vertical) than a foot flat runner.

To analyze the sprint foot in function, an alignment change of the calf shank and foot keel is made. Advantage is taken of the foot keel having all of its concavities with their longitudinal axis orientation parallel to the frontal plane. The calf shank is plantar flexed and slid posterior on the foot keel. This lowers the distal circles even further than on the flat foot runner with the multi-use foot keel like that in FIGS. 3-5 and 8, for example. As a consequence, there is even greater horizontal motion potential and the dynamic response is directed into this improved horizontal capability.

The sprinters have increased range of motion, forces and momentum (inertia)—momentum being a prime mover. Since their stance phase deceleration phase is shorter than their acceleration phase, increased horizontal linear velocities are achieved. This means that at initial contact, when the toe touches the ground, the ground pushes posteriorly on the foot and the foot pushes anteriorly on the ground. The calf shank which has increased forces and momentum is forced into even greater flexion and downward movement than the initial contact foot flat runner. As a consequence to these forces, the foot's long arch concavity is loaded by expansion and the calf shank is loaded by expansion. These expansion forces are resisted to a greater extent than all the other previously mentioned forces associated with running. As a consequence, the dynamic response capability of the foot is proportional to the force applied. The human tibia fibula calf shank response is only associated with the energy force potential—it is a straight structure and it cannot store energy. These expansion forces in the prosthetic foot of the invention in sprinting are greater in magnitude than all the other previously mentioned forces associated with walking and running. As a consequence, the dynamic response capability of the foot is proportional to the applied forces and increased amputee athletic performance, as compared with human body function, is possible.

Figure 25:
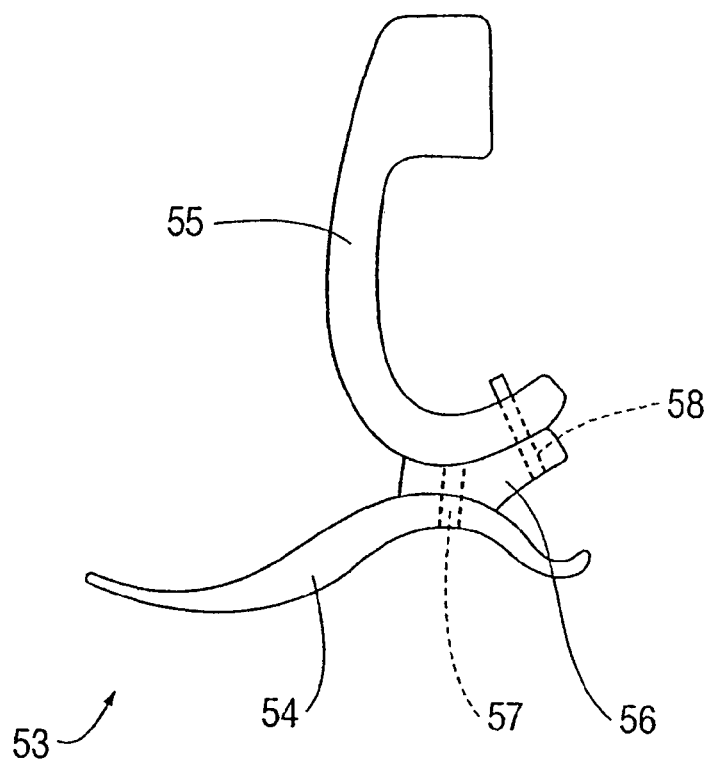
FIG. 25 is a side view of another prosthetic foot of the invention similar to that in FIG. 3, but showing use of a coupling element with two releasable fasteners spaced longitudinally connecting the element to the calf shank and foot keel, respectively.
Figure 26:
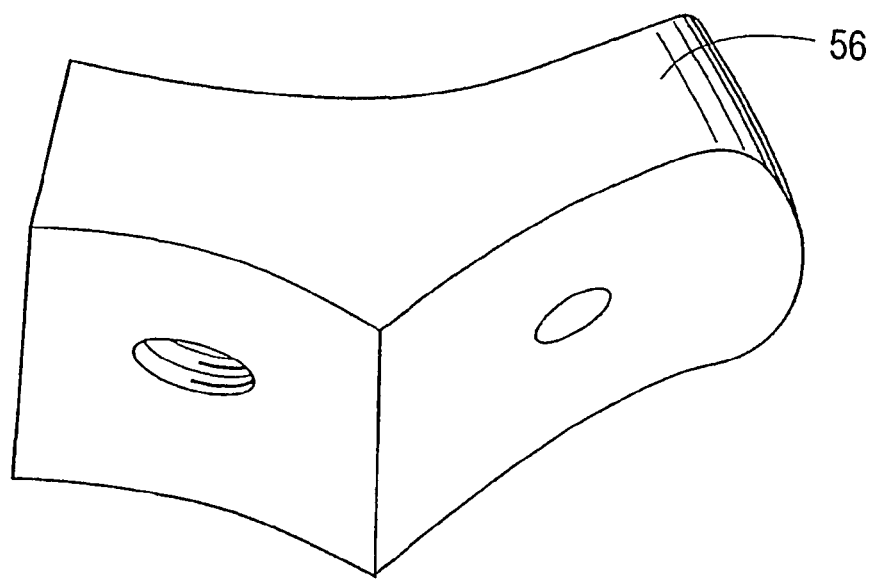
FIG. 26 is an enlarged side view of the coupling element in FIG. 25.
Figure 27:
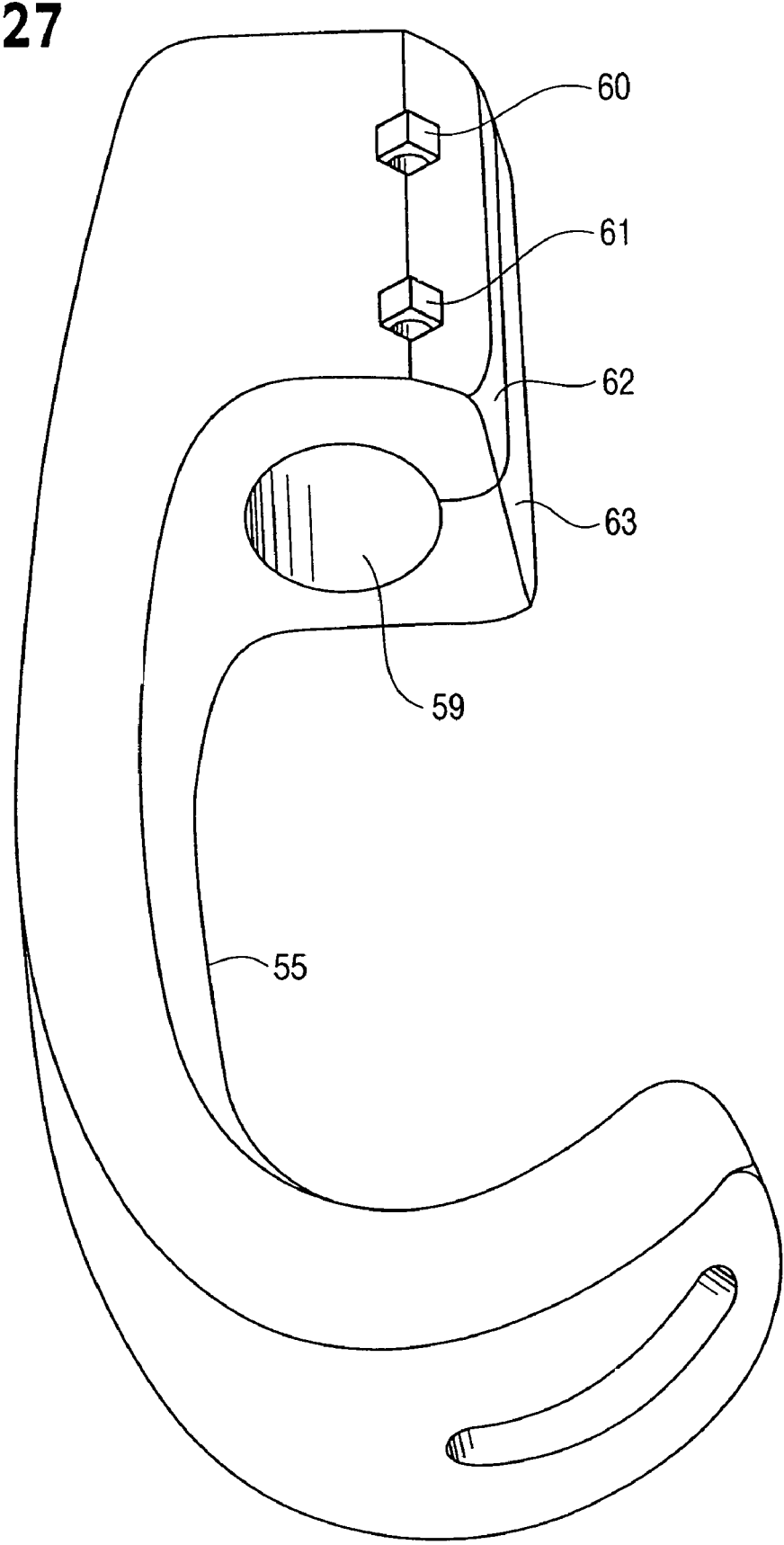
FIG. 27 is an enlarged side view of the calf shank of the prosthetic foot of FIG. 25.

The prosthetic foot 53 depicted in FIG. 25 is like that in FIG. 3 except for the adjustable fastening arrangement between the calf shank and the foot keel and the construction of the upper end of the calf shank for connection to the lower end of a pylon. In this example embodiment, the foot keel 54 is adjustably connected to the calf shank 55 by way of plastic or metal alloy coupling element/ankle coupler 56. The coupling element Is attached to the foot keel and calf shank by respective releasable fasteners 57 and 58 which are spaced from one another in the coupling element in a direction along the longitudinal direction of the foot keel. The fastener 58 joining the coupling element to the calf shank is more posterior than the fastener 57 joining the foot keel and the coupling element. By increasing the active length of the calf shank in this way, the dynamic response capabilities of the calf shank itself are increased. Changes in alignment are made in cooperation with longitudinally extending openings in the calf shank and foot keel as in other example embodiments.

The upper end of the calf shank 55 is formed with an elongated opening 59 for receiving a pylon 15. Once received in the opening, the pylon can be securely clamped to the calf shank by tightening bolts 60 and 61 to draw the free side edges 62 and 63 of the calf shank along the opening together. This pylon connection can be readily adjusted by loosening the bolts, telescoping the pylon relative to the calf shank to the desired position and reclamping the pylon in the adjusted position by tightening the bolts.

The prosthetic foot 70 shown in FIGS. 28-32 is similar to those in FIGS. 3-5, 8, 23 and 24 and FIGS. 25-27, but further includes a calf shank range of motion limiter and dampener device 71 on the foot to limit the extent of the motion of the upper end of the calf shank with force loading and unloading of the calf shank during use of the foot by the amputee. This feature is especially useful in a prosthetic foot having a relatively long calf shank where the wearer is to engage in activities such as running and jumping that generate forces in the calf shank many times the wearer's body weight, e.g., with running 5-7 times body weight and jumping 11-13 times body weight. In contrast, the forces generated in walking are only 1-1 ½ times body weight.

The device 71 in the example embodiment is a two-way acting piston cylinder unit in which pressurized fluids, a gas such as air or a hydraulic liquid, are provided through respective fittings 73 and 74. The device has two variable controls, one for compression, one for expansion, which permit adjustment of the permissible extent of the motion of the upper end of the calf shank in both compression and expansion of the calf shank in force loading and unloading. The device 71 also dampens the energy being stored or released during calf shank compression and expansion. The opposite ends of the piston-cylinder device 71 are connected to the upper end of the calf shank and the lower portion of the foot, and preferably in the example embodiment to respective ends of the calf shank at pivot connections 75 and 76 which are preferably ball joints.

Figure 31:
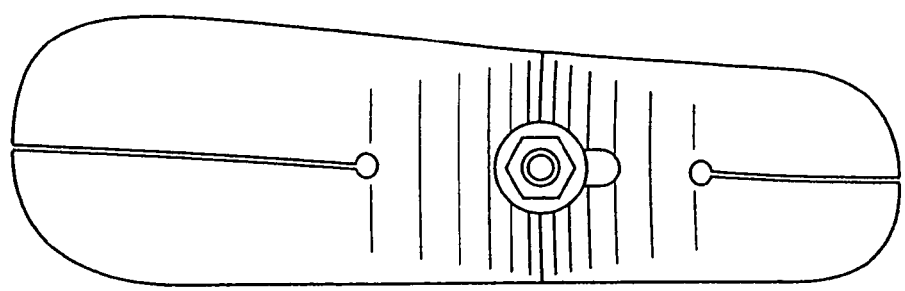
FIG. 31 is a bottom view of the prosthetic foot of FIG. 28.
Figure 32:
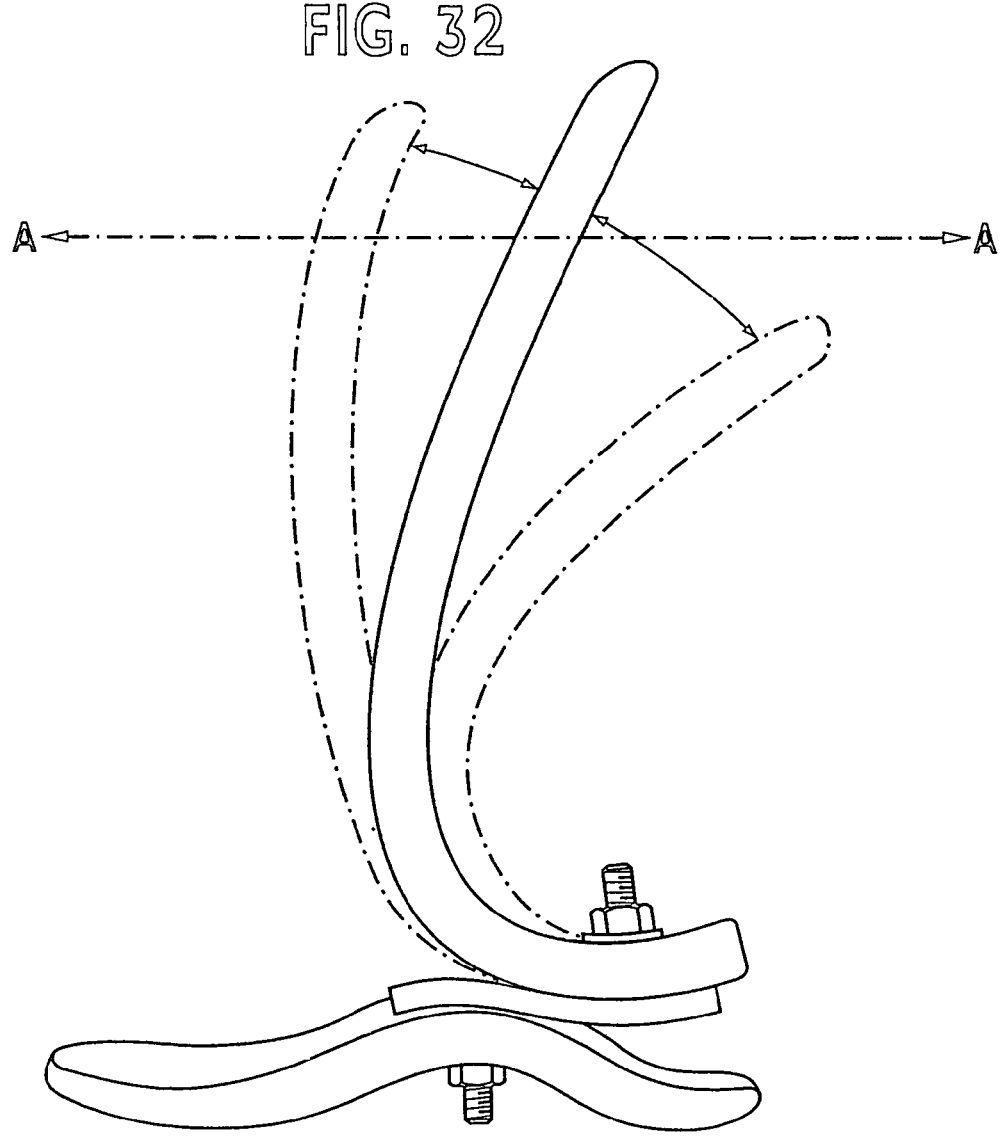
FIG. 32 is a side view of the calf shank and foot keel of the prosthetic foot of FIG. 28 illustrating an example of the motion of the upper end of the calf shank resulting from force loading and unloading the calf shank during use of the prosthetic foot.

The motion of the upper end of the calf shank 72 of the foot 70 in compression and expansion of the calf shank is depicted in FIG. 32. The generally parabola shape of the calf shank is such that the upper end of the calf shank can move longitudinally with respect to the foot keel 77 and lower end of the calf shank connected thereto, e.g., along direction A-A in FIGS. 5 and 32, with compression and expansion of the calf shank in force loading and unloading thereof. Thus, the improved dynamic response capabilities of the prosthetic foot are retained in the example embodiment of FIGS. 28-32.

The device 71 is not limited to the described piston cylinder unit but could be another velocity control and/or motion limiting device. For example, it is envisioned that the posterior range of motion limiting dampening device 71 employed on the calf shank of the prosthetic foot could be a microprocessor-controlled hydraulic unit with compression and expansion phase control, such as those now used for controlling motion in artificial knee joints. In such case, on-board sensors are provided that read and adapt to the individual's movements. By using special software and a PC, fine adjustments can be made to tailor the microprocessor controlled hydraulic unit to the amputee. Moments can be measured as much as 50 times per second—ensuring the dynamic gait is as similar to natural walking as possible. Because of the responsiveness of the hydraulic unit, it is suitable for a broad spectrum of lower limb amputees. A lithium-ion battery loaded in the unit provides enough energy to operate the hydraulic unit for a full day. The resistance for compression is adjusted independent of the expansion adjustments. Multiple integrated sensors stream gait analysis data to the on-board microprocessor that automatically adjusts the stance and swing phase characteristics of the unit 50 times per second.

This microprocessor controlled hydraulic unit of device 71 is more responsive than a mechanical hydraulic unit. An electrically controlled compression (plantar flexion) valve, adjusts 50 times per second. The compression valve in the unit is automatically fully opened during pre-swing. As a result, the unit is extremely easy to compress flex at slow speeds, in confined areas, and under similar conditions. The speed of the servo motor of the unit allows it to close the compression (plantar flexion) and expansion dorsiflexion valves very rapidly, in response to the microprocessor commands sent 50 times per second. When the valves are nearly closed, the unit dampening force becomes very high, making rapid walking and even running possible. The unique prosthesis-adjustable dynamic factor allows the hydraulic unit to be optimized for all gait patterns from slow to aggressive, fast gait speeds and movements. This ability to "tune" a microprocessor controlled hydraulic unit to the individual's unique gait pattern enables a wide range of cadences to be obtained in the prosthetic foot with high gait efficiency and comfort. That is, the use of a microprocessor hydraulic unit as the device 71 enhances the variable cadence required when the prosthetic foot is utilized by active amputees.

Figure 29:
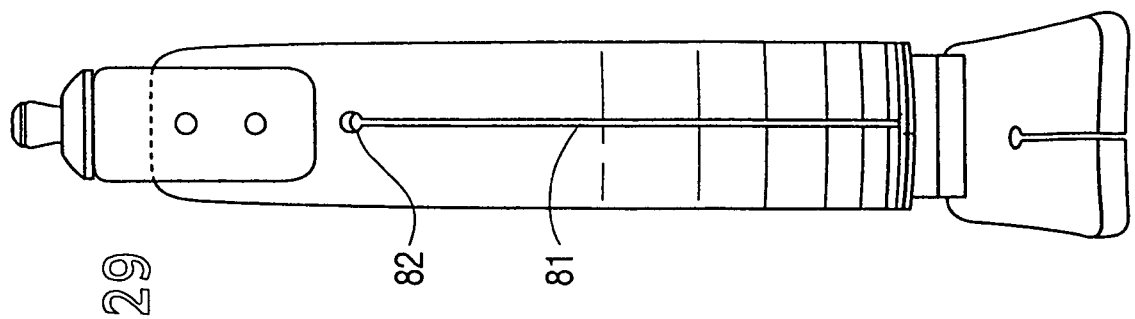
FIG. 29 is a front view of the prosthetic foot as seen from the left side of the prosthetic foot depicted in FIG. 28 showing a longitudinal slot in the calf shank of the foot.
Figure 28:
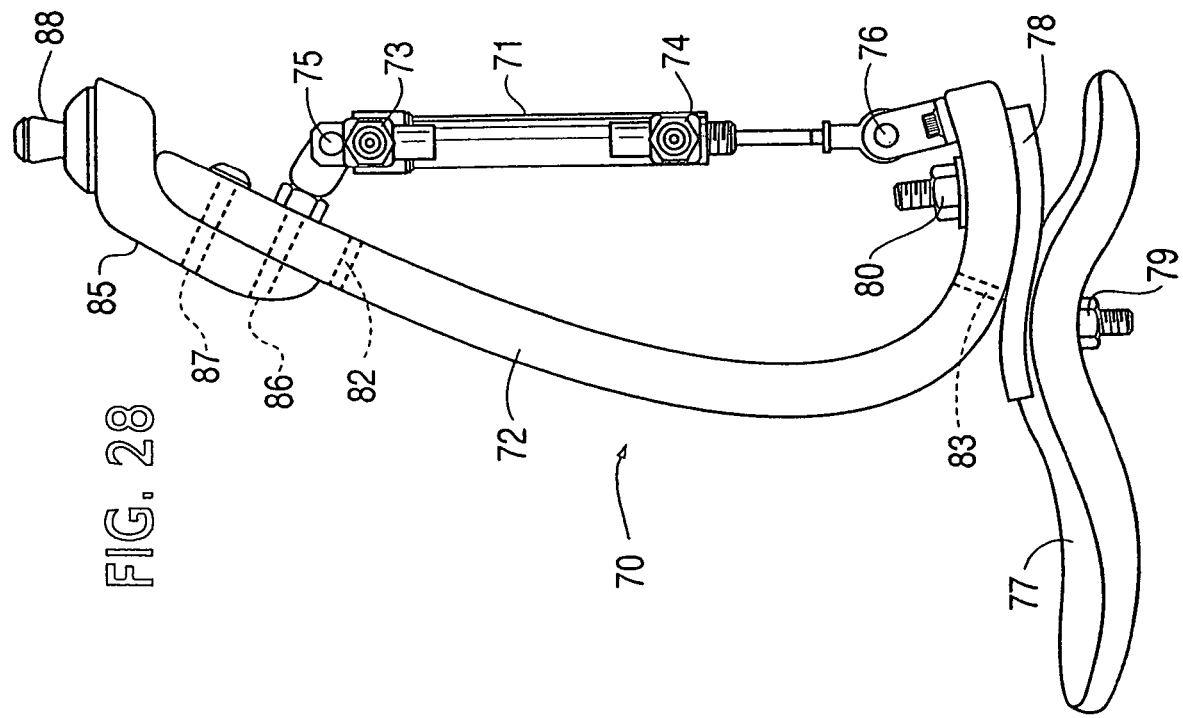
FIG. 28 is a side view of a further example embodiment of the prosthetic foot similar to those in FIGS. 3 and 25 wherein a motion limiting, dampening device is connected between respective ends of the calf shank to limit the extent of the motion of the upper end of the calf shank in response to force loading and unloading the calf shank during use of the prosthetic foot.
Figure 30:
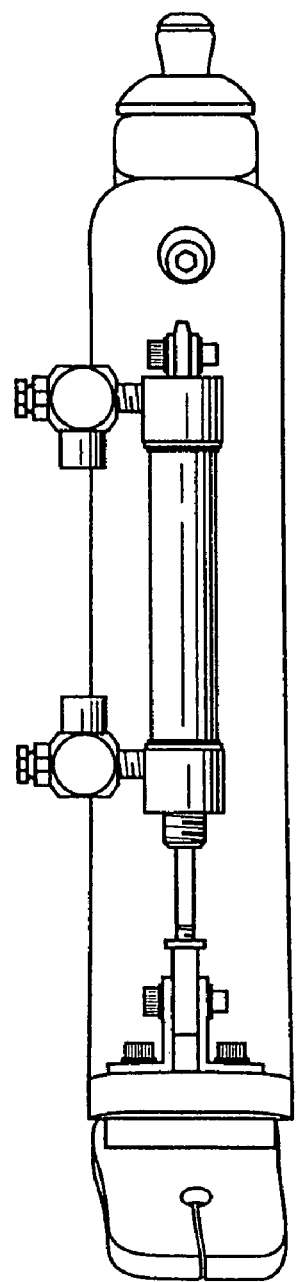
FIG. 30 is a rear view of the prosthetic foot, as seen from the right side of the prosthetic foot shown in FIG. 28.

The longitudinally extending foot keel 77 of the prosthetic foot 70 in FIGS. 28-32 has forefoot, midfoot and hindfoot portions like the foot keels in FIGS. 3 and 25. The calf shank 72 of the foot is attached to the foot keel by a coupling element/ankle coupler 78 with two releasable fasteners 79 and 80 spaced longitudinally connecting the coupling element to the calf shank and foot keel, respectively, as in the example embodiment of FIGS. 25-27. The calf shank 72 Includes a longitudinally extending expansion slot 81 intermediate the ends of the calf shank. Expansion joint holes 82 and 83 are located at the ends of the expansion slot. The forefoot and hindfoot portions of the foot keel are also formed with respective expansion slots as seen in FIGS. 29, 30 and 31.

A prosthetic socket attached to the amputee's lower leg stump is connected to the upper end of calf shank 72 via an adapter 85 secured to the upper end of the calf shank by fasteners 86 and 87 as shown in the drawings. The adapter has an inverted pyramid-shaped attachment fitting 88 connected to an attachment plate attached to an upper surface of the adapter. The pyramid fitting is received by a complementarily shaped socket-type fitting on the depending prosthetic socket for joining the prosthetic foot and prosthetic socket. This type of connection is shown in the embodiment of FIGS. 34-36.

Figure 33:
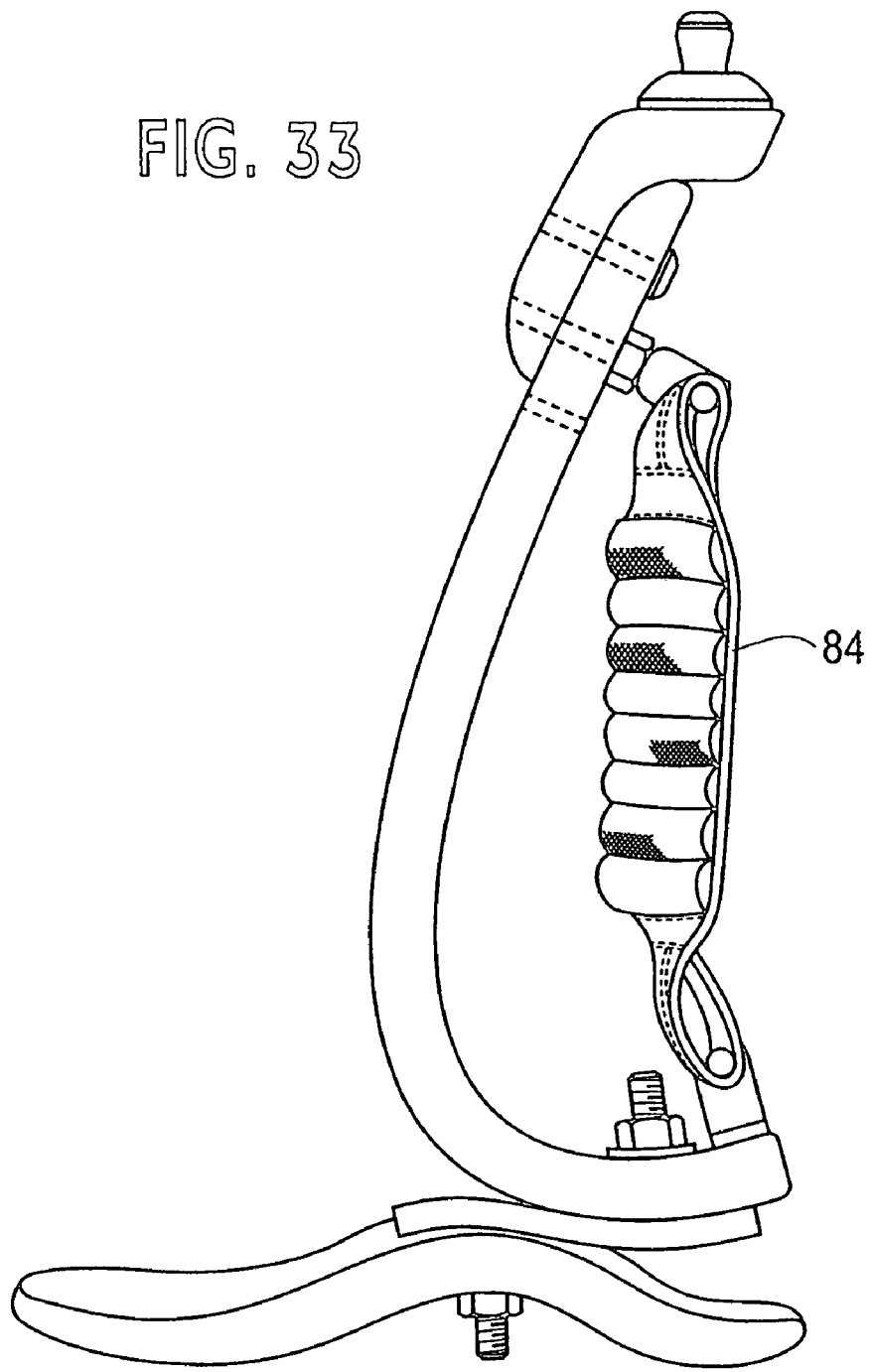
FIG. 33 is a side view of a still further example embodiment of the prosthetic foot like that in FIGS. 28-32 except that a flexible strap is used to limit only the extent of expansion motion of the upper end of the calf shank.

While the motion limiting, dampening device 71 in the example embodiment of FIGS. 28-32 limits the extent of the motion of the upper end of the calf shank in both compression and expansion of the calf shank, a similar device which only limits the extent of motion of the upper end of the calf shank in one of compression and expansion could be employed. A motion limiting, dampening device 84 restricting only the expansion of the upper end of the calf shank with forced loading and unloading is shown in the example embodiment of FIG. 33. The device 84 therein is a flexible strap which allows limited, elastic extension of the strap and thereby expansion of the calf shank while not limiting the motion of the upper end of the calf shank in compression loading of the calf shank.

Figure 36:
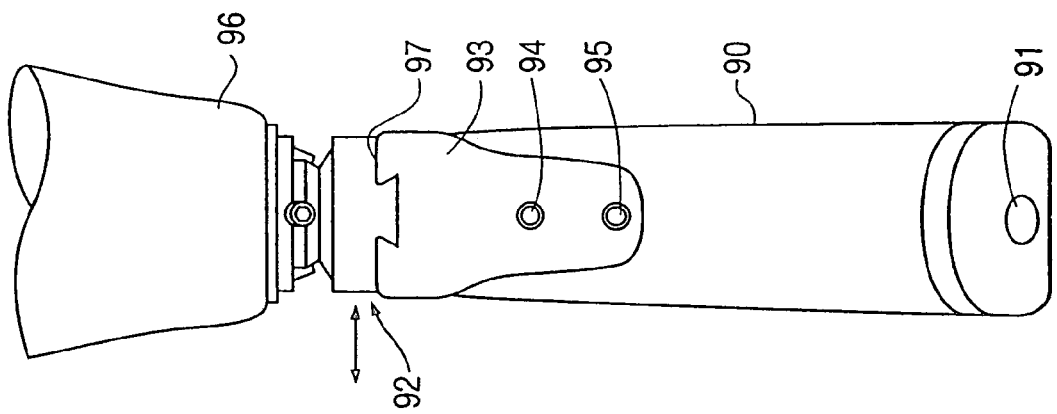
FIG. 36 is a rear view of the prosthetic foot of FIG. 34, as seen from the right side of the foot in FIG. 34.
Figure 35:
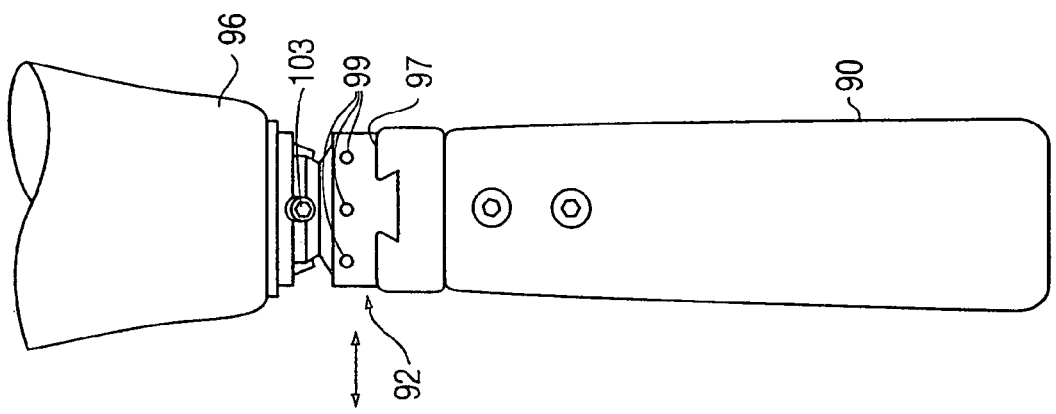
FIG. 35 is a front view of the prosthetic foot of FIG. 34, as seen from the left side of the foot as shown in FIG. 34.
Figure 34:
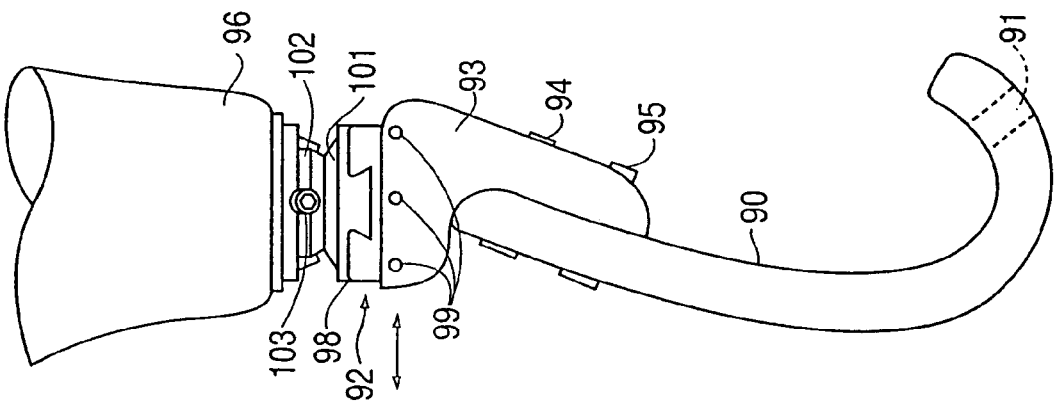
FIG. 34 is a side view of another embodiment of the prosthetic foot with an alignment coupler device located on an adapter connected to the upper end of the calf shank for securing the foot to a prosthetic socket attached to an amputee's leg, the alignment coupler device allowing medial-lateral and anterior-posterior sliding adjustment of the foot relative to the prosthetic socket.

FIGS. 34-36 illustrate another calf shank 90 of the invention which can be used with the foot keel 77 of the prosthetic foot in FIGS. 28-32 or with one of the other foot keels disclosed herein. The calf shank 90 has generally parabola shape with the smallest radius of curvature thereof located at the lower end and extending upwardly, and initially anteriorally into relatively larger radii at the proximal terminal end thereof. A posterior facing concavity is formed by the curvature of the calf shank as depicted in FIG. 34. The distal end of the calf shank has a longitudinally extending opening 91 which, together with coupling element 78, releasable fasteners 79 and 80 and a longitudinally extending opening in the foot keel permit adjusting the alignment of the calf shank and the foot keel with respect to one another in the longitudinal direction when the fastener 79 or 80 is loosened or released for tuning the performance of the prosthetic foot to be task specific.

The distal end of the calf shank 90 is more sharply curved, e.g., has a smaller radius of curvature, than the calf shank 72 in FIGS. 28-32, and extends upwardly and anteriorly in a shorter longitudinal distance. This calf shank shape is more cosmetically friendly. That is, its distal end is located more in the ankle region, where the medial and lateral malleoli of a human foot shaped outer covering of the prosthetic foot would normally be located. The calf shank tucks in the outer prosthetic foot covering better. Its functional characteristics are that it responds quicker to initial contact ground reaction forces, although with less dynamic response capability than a calf shank with a wider parabola, e.g., longer radii of curvature as noted above. Thus, those active persons who run and jump with a prosthetic foot would benefit from using a wider parabola or radius of curvature which affords a greater horizontal velocity.

The calf shank 90 of FIGS. 34-36 further includes an alignment coupler device 92 located intermediate a plastic or metal adapter 93 connected to the upper end of the calf shank by fasteners 94 and 95. and the lower end of a prosthetic socket 96 secured to the leg stump of the user. The user could be an above the knee or a below the knee amputee, for example. The alignment coupler device contains a pair of slides 97 and 98 arranged at right angles to each other and in planes parallel to the ground. The relative position of the components of each slide can be adjusted by loosening threaded fasteners 99 for adjusting the respective slides 97 and 98 to change the relative orientation of the prosthetic socket to the calf shank and foot keel of the prosthetic foot. The top of the adapter 93 supporting the device 92 is preferably parallel to the ground in the stance phase of gait with the prosthetic foot.

The top of the upper slide 98 of the device 92 has an inverted pyramid shaped fitting 101 secured thereon which is adjustably clamped in a corresponding fitting 102 on the prosthetic socket 96 by means of threaded fasteners 103. This connection between fitting 101 and 102 allows for angular change-flexion/extension and abduction/adduction between the prosthetic socket and foot. The slides of device 92 allow medial-lateral and anterior-posterior linear, sliding adjustments. Thus, the device 92 is an alignment fixture which allows the prosthetic socket to be moved in all directions, which influences how the ground reaction forces respond to the calf shank and foot keel mechanical structures.

Figure 37:
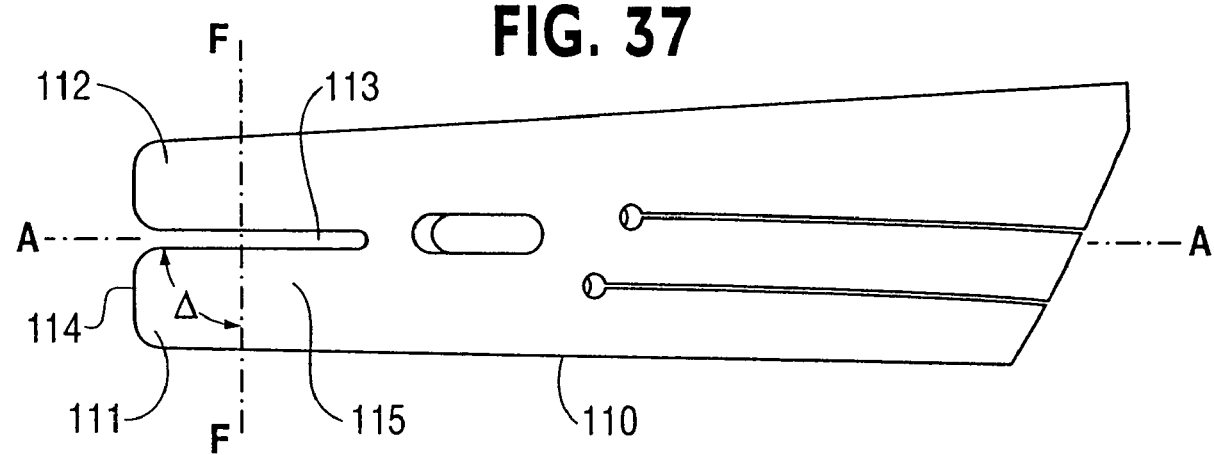
FIG. 37 is a top view of another foot keel for a prosthetic right foot of the invention wherein the posterior end of the foot is parallel to the frontal plane, e.g., perpendicular to the longitudinal axis A-A of the foot, and the longitudinal axis F-F of a proximal hindfoot concavity is also perpendicular to the longitudinal axis A-A.
Figure 38:
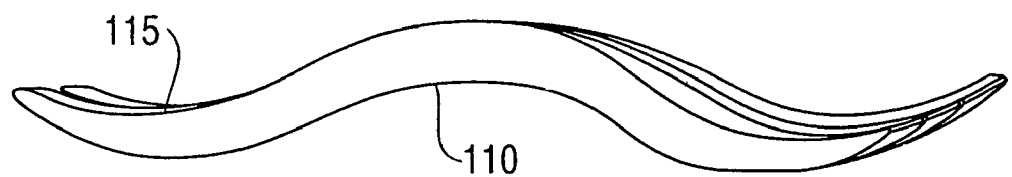
FIG. 38 is a side of the foot keel of FIG. 37 as seen in the direction from the lateral side of the foot keel.
Figure 39:
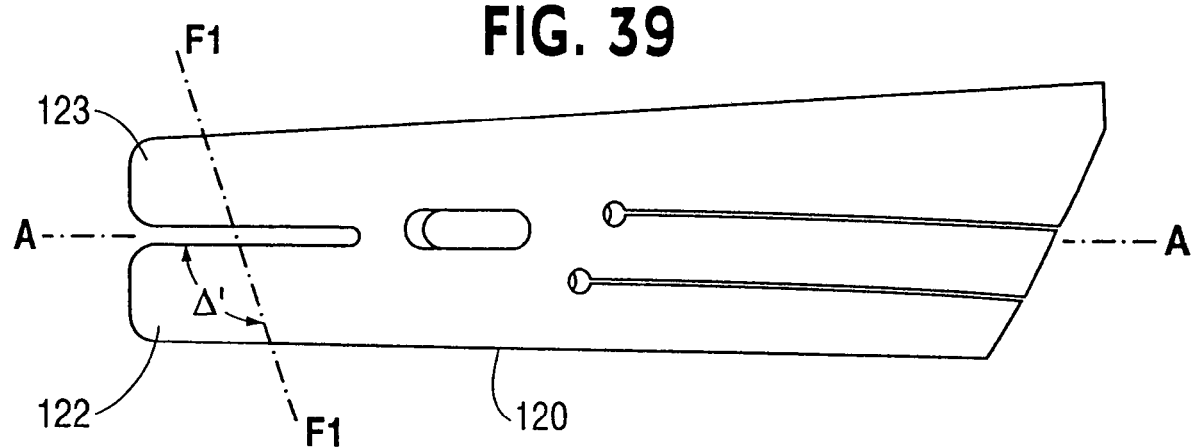
FIG. 39 is a top view of an additional foot keel of the invention similar to that in FIGS. 37 and 38, but having a longitudinal axis F'-F' of its proximal hindfoot concavity at an obtuse angle $\Delta'$ to the longitudinal axis A-A which renders the lateral strut of the hindfoot effectively longer and more flexible than the medial strut to aid eversion of the foot on heel contact in gait.
Figure 40:
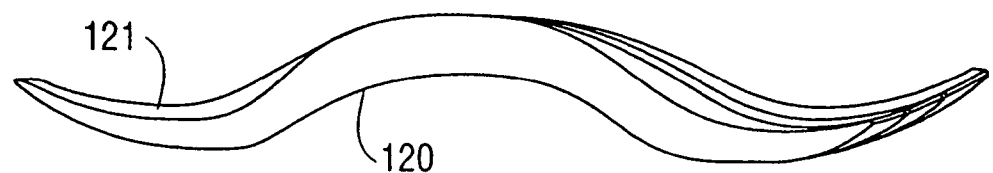
FIG. 40 is a side view of the foot keel of FIG. 39 as seen from the lateral side of the foot keel.

The foot keel 110 in FIGS. 37 and 38 and the foot keel 120 of FIGS. 39 and 40 are further example embodiments foot keels which can be used in the prosthetic foot of the invention. The foot keels are for the right foot and have similar constructions except in the hindfoot portion. The medial and lateral sides of the two foot keels are the same shape. Foot keel 110 is sagittally cut in the hindfoot area with identical lateral and medial expansion struts 111 and 112 separated by a longitudinally extending expansion joint or slot 113. The posterior terminal heel area 114 of the foot keel 110 is parallel to the frontal plane, e.g., perpendicular to the longitudinal axis A-A of the foot keel. Similarly, the hindfoot dorsal concavity 115 of the foot keel has its longitudinal axis F-F parallel to the frontal plane, e.g., at right angles to the longitudinal axis A-A, i.e., angle $\Delta$ is 90°.

Foot keel 120, in contrast to foot keel 110, is not sagittally cut in the hindfoot area but has its hindfoot dorsal concavity 121 cut such that the longitudinal axis F'-F' of the concavity is skewed transverse to the frontal plane, e.g., makes an obtuse angle $\Delta'$ with the longitudinal axis A-A of preferably 110-125° with the lateral side further anterior than the medial side. This orientation of the dorsal concavity makes the lateral expansion strut 122 thinner over a greater length than the medial expansion strut 123, and thereby effectively longer and more flexible than strut 123. This increase in flexibility predisposes the hindfoot to respond to initial contact ground reaction forces by everting—which is a shock absorption mechanism. This aids in efficiently transferring the forces of the body's center of gravity through the hindfoot of the foot keel in gait for achieving a more normal gait pattern.

This concludes the description of the example embodiments. Although the present invention has been described with reference to a number of illustrative embodiments, it should be understood that numerous other modifications and embodiments can be devised by those skilled in the art that will fall within the spirit and scope of the principles of this invention. For example, the lower end of the calf shank in the prosthetic foot of the invention is not limited to a parabola shape or a generally parabola shape but can be otherwise downward convexly, curvilinearly configured to produce the desired motion outcomes of the foot when connected to the foot keel to form the ankle joint area of the foot. The features of the various embodiments could also be used with one another. More particularly, reasonable variations and modifications are possible in the component parts and/or arrangements of the subject combination arrangement within the scope of the foregoing disclosure, the drawings, and the appended claims without departing from the spirit of the invention. In addition to variations and modifications in the component parts and/or arrangements, alternative uses will also be apparent to those skilled in the art.

What is claimed is:

1. A prosthetic foot comprising:
a longitudinally extending foot keel having forefoot, midfoot and hindfoot portions;
a resilient, upstanding, monolithically formed shank having a lower end connected to the midfoot portion of the foot keel and posteriorly terminating in a free end, the shank extending upwardly from the foot keel to a middle portion of the shank by way of an initially downward and anterior facing continuous convexly curved surface to form an ankle joint area of the prosthetic foot and extending upwardly in a substantially anterior facing convexly curvilinear manner above the ankle joint area to a substantially vertically oriented upper end to form a lower, prosthetic part of a leg for connection with a supporting structure on a person's leg stump, wherein the width of the resilient shank in the frontal plane of the prosthetic foot is greater than the thickness of the shank in the sagittal plane throughout the entire length of the shank such that both the ankle joint area and the prosthetic part of a leg formed by the shank are compressible and expandable in the longitudinal direction in response to the ground reaction force thereon during gait with the upper end of the shank moving posteriorly in plantarflexion and anteriorly in dorsiflexion for storing and releasing energy to improve dynamic response of the prosthetic foot in gait; and
a device extending between and connected to the upper and lower ends of the shank to dampen the motion and limit the extent of the upper end of the shank in at least one of compression and expansion.

2. The prosthetic foot according to claim 1, wherein the device limits the anterior motion of the upper end of the shank.

3. The prosthetic foot according to claim 2, wherein the device also limits the posterior motion of the upper end of the shank.

4. The prosthetic foot according to claim 1, wherein the device includes a piston-cylinder containing at least one pressurized fluid.

5. The prosthetic foot according to claim 1, wherein the device includes a microprocessor controlled hydraulic unit.

6. The prosthetic foot according to claim 1, wherein the device includes a flexible strap allowing limited elastic extension, the strap extending between and connected to respective ends of the shank.

7. The prosthetic foot according to claim 1, wherein the shank includes a longitudinally extending expansion slot intermediate the ends of the calf shank.

8. The prosthetic foot according to claim 7, wherein the shank further includes an expansion joint hole located at each end of the expansion slot.

9. The prosthetic foot according to claim 1, wherein at least one of the foot keel and the shank is formed of a laminated composite material including reinforcing fiber laminated with polymer matrix material.

10. The prosthetic foot according to claim 9, wherein the polymer matrix material is a thermoplastic material.

11. The prosthetic foot according to claim 9, wherein the laminated composite material is thermo-formed.

12. The prosthetic foot according to claim 9, wherein the polymer matrix material is a thermosetting material.

13. The prosthetic foot according to claim 1, wherein the lower end of the shank is downward convexly curved.

14. The prosthetic foot according to claim 13, wherein the convexly curved lower end of the shank has a radius of curvature which increases as the shank extends upwardly from its curved lower end.

15. The prosthetic foot according to claim 1, further comprising an alignment coupler device connected to the upper end of the shank, the device having a fitting to connect with a supporting structure on a person's leg stump and adjustable slide mechanisms to adjust the foot medial/lateral and anterior/posterior position with respect to the fitting and a supporting structure to which it is connected.

16. The prosthetic foot according to claim 15, further comprising an adapter connecting the alignment coupler device and the upper end of the shank.

17. The prosthetic foot according to claim 1, wherein the hindfoot of the foot keel has a dorsal concavity with a longitudinal axis skewed with respect to the frontal plane such that the lateral side of the concavity is further anterior than the medial side.

18. The prosthetic foot according to claim 1, wherein the plantar surface of the midfoot portion of the foot keel has a longitudinal arch concavity with a medial aspect larger in radius than a lateral aspect.

19. The prosthetic foot according to claim 1, further comprising an adjustable fastening arrangement connecting the lower end of the shank to the foot keel to form the ankle joint area, the fastening arrangement permitting adjustment of the alignment of the shank and the foot keel to one another in the longitudinal direction of the foot for tuning the performance of the prosthetic foot.

20. The prosthetic foot according to claim 19, wherein the adjustable fastening arrangement includes at least one releasable fastener and a coupling element located between the shank and the foot keel.

21. The prosthetic foot according to claim 1, wherein the lower end of the shank is connected to the foot keel by way of a coupling element.

22. The prosthetic foot according to claim 1, wherein the lower end of the shank is downward convexly curved and is generally parabola shaped with the smallest radius of curvature thereof located at the lower end and extending therefrom.

23. The prosthetic foot according to claim 22, wherein the lower end of the shank includes means for adjustably positioning the lower end with respect to the longitudinal direction of the foot keel.

24. The prosthetic foot according to claim 1, wherein the lower end of the shank is connected to the foot keel by way of an ankle coupler which is connected to respective ones of the shank and foot keel at longitudinally spaced connections.

25. The prosthetic foot according to claim 1, wherein the posterior terminal end extends upwardly.

26. A shank for a prosthetic foot comprising:
an elongated, semi-rigid, monolithically formed, resilient member having a lower end to connect with a longitudinally extending foot keel of the prosthetic foot with the lower end posteriorly terminating in a free end with the member extending upwardly from the foot keel by way of an initially downward and anterior facing continuous convexly curved surface to form an ankle joint area of the prosthetic foot and extending upwardly in a substantially anterior facing convexly curvilinear manner above the ankle joint area to a substantially vertically oriented upper end to form a lower prosthetic part of a leg for connection with a supporting structure on a person's leg stump, wherein the member has a width in the frontal plane of the prosthetic foot which is greater than the thickness of the member in the sagittal plane throughout the entire length of the member such that when the one lower end is connected to the foot keel, the member can be flexed in compression and expansion in response to force loading and unloading of the shank during use of the prosthetic foot such that the upper end of the member moves longitudinally with respect to the foot keel; and
a device extending between and connected to the upper and lower ends of the member for dampening the motion and limiting the extent of the motion of the upper end of the member in at least one of compression and expansion during use thereof in a prosthetic foot.

27. The shank according to claim 26, wherein the device limits the anterior motion of the upper end of the member.

28. The shank according to claim 27, wherein the device also limits the posterior motion of the upper end of the shank.

29. The shank according to claim 26, wherein the device includes a piston-cylinder containing at least one pressurized fluid.

30. The shank according to claim 26, further comprising an alignment coupler device connected to the upper end of the shank, the device having a fitting to connect with a supporting structure on a person's leg stump and adjustable slide mechanisms to adjust the foot medial/lateral and anterior/posterior position with respect to the fitting and a supporting structure to which it is connected.

31. The shank according to claim 30, further comprising an adapter connecting the alignment coupler device and the upper end of the shank.

32. The shank according to claim 30, wherein said fitting to connect with a supporting structure on a person's leg stump allows for angular change flexion/extension and abduction/adduction between the supporting structure and the prosthetic foot.

33. The shank according to claim 26, wherein the device includes a flexible strap which allows limited, elastic extension, the strap extending between and connected to respective ends of the member.

34. The shank according to claim 26, wherein the member includes a longitudinally extending expansion slot intermediate the ends thereof.

35. The shank according to claim 34, wherein the member further includes an expansion joint hole located at each end of the expansion slot.

36. The shank according to claim 26, wherein the resilient member is formed of a laminated composite material including reinforcing fiber laminated with polymer matrix material.

37. The shank according to claim 36, wherein the polymer matrix material is a thermoplastic material.

38. The shank according to claim 36, wherein the polymer matrix material is a thermosetting material.

39. The shank according to claim 36, wherein the laminated composite material is thermo-formed.

40. The shank according to claim 26, wherein the one end of the member is outward convexly curved.

41. The shank according to claim 40, wherein the outward convexly curved one end of the resilient member is generally parabola shaped with the smallest radius of curvature thereof located at the one end and extending therefrom.

42. The shank according to claim 26, wherein the one end of the member includes means for adjustably positioning the one end with respect to the longitudinal direction of a foot keel to which the shank is to be attached.

43. The shank according to claim 26, wherein the device includes a flexible strap which allows tensioned flexion, the strap extending between and connected to respective ends of the member.

44. A prosthetic foot comprising:

a longitudinally extending foot keel having forefoot, midfoot and hindfoot portions;

a resilient, upstanding, monolithically formed shank having a lower end connected to the midfoot portion of the foot keel and posteriorly terminating in a free end, the shank extending upwardly from the foot keel to a middle portion of the shank by way of an initially downward and anterior facing continuous convexly curved surface to form an ankle joint area of the prosthetic foot and extending upwardly in a substantially anterior facing convexly curvilinear manner above the ankle joint area to a substantially vertically oriented upper end to form a lower, prosthetic part of a leg for connection with a supporting structure on a person's leg stump, wherein the width of the resilient shank in the frontal plane of the prosthetic foot is greater than the thickness of the shank in the sagittal plane throughout the entire length of the shank such that both the ankle joint area and the prosthetic part of leg formed by the shank are compressible and expandable in the longitudinal direction in response to the ground reaction force thereon during gait with the upper end of the shank moving posteriorly in plantarflexion and anteriorly in dorsiflexion for storing and releasing energy to improve dynamic response of the prosthetic foot in gait; and a device extending between and connected to the upper and lower ends of the shank which elastically resists anterior movement of the upper end of the calf shank with respect to the foot keel

45. The prosthetic foot according to claim 44, wherein the device limits the extent of anterior movement of the upper end of the shank relative to the foot keel.

46. A shank for a prosthetic foot comprising: an elongated, semi-rigid, monolithically formal resilient member having one, lower end to connect with a longitudinally extending foot keel of the prosthetic foot, the lower end posteriorly terminating in a free end with the member extending upwardly from the lower end by way of an initially downward and anterior facing convexly curved surface to form an ankle joint area of the prosthetic foot and extending upwardly in a substantially anterior facing convexly curvilinear manner above the ankle joint area to a substantially vertically oriented upper end to form a lower prosthetic part of a leg for connection with a supporting structure on a person's leg stump, wherein the member has a width in the frontal plane of the prosthetic foot which is greater than the thickness of the member in the sagittal plane throughout the entire length of the member, such that when the one, lower end is connected to the foot keel, the member can be flexed in response to force loading and unloading of the shank during use of the prosthetic foot such that the opposite, upper end of the member moves relative to the foot keel; and a device extending between and connected to the upper and lower ends of the shank for elastically resisting anterior movement of the upper end of the shank with respect to the foot keel in the prosthetic foot.

47. The shank according to claim 46, wherein the device limits the extent of anterior movement of the upper end of the shank relative to the foot keel.

48. A method of generating kinetic power for propulsive force in a lower extremity prosthesis including a foot, an ankle and an elongated, upstanding shank above the ankle, the method comprising:

providing a monolithically formed resilient member which forms the ankle and the shank in the prosthesis with the resilient member having a lower end posteriorly terminating in a free end and extending upwardly from the foot by way of an initially downward and anterior facing continuous convexly curved surface to form the ankle and in the area of the shank extending upwardly in a substantially anterior facing convexly curvilinear manner to a substantially vertically oriented upper end connected with a supporting structure on a person's leg stump, the resilient member of the ankle and the shank having a width in the frontal plane of the prosthesis which is greater than the thickness in the sagittal plane throughout the entire length of the member so as to be compressible and expandable in the longitudinal direction in response to the ground reaction force thereon during gait with the upper end moving posteriorly in plantarflexion and anteriorly in dorsiflexion for storing and releasing energy to improve the dynamic response of the prosthesis in gait; and controlling the dynamic response capability of the resilient member for movement of the upper end of the member in the longitudinal direction with respect to the foot in force loading and unloading of the prosthesis in gait, posteriorly in plantarflexion and anteriorly in dorsiflexion, for storing and releasing energy to improve dynamic response of the prosthesis in gait.

49. The method according to claim 48, wherein said controlling includes adjustably selecting the alignment of the shank relative to the foot in the longitudinal direction of the foot.

50. The method according to claim 48, wherein said controlling includes adjustably selecting an active length of the shank in the prosthesis.

51. The method according to claim 48, wherein said controlling includes limiting the extent of the motion of the upper end of the resilient member.

52. The method according to claim 48, wherein said controlling includes limiting the anterior motion of the upper end of the resilient member.

53. The method according to claim 48, wherein said controlling includes limiting the posterior motion of the upper end of the resilient member.

54. The method according to claim 48, wherein said controlling includes storing elastic energy with a device on the prosthesis during force loading of the prosthesis and releasing the stored energy adding to the propulsion of the user during force unloading.

55. The method according to claim 54, wherein said device is a flexible strap which allows limited, elastic extension of the strap with force loading of the prosthesis in gait.

56. The method according to claim 48, further comprising providing the foot in the prosthesis with a high low dynamic response capability.

57. A method of generating kinetic power for propulsive force in a prosthetic foot comprising:

providing a prosthetic foot having a longitudinally extending foot keel attached to a resilient monolithically formed shank which forms an ankle and a lower prosthetic part of a leg for connection with a lower extremity prosthetic socket on a person's leg stump, the shank including a lower end posteriorly terminating in a free end and extending upwardly from the foot keel by way of an initially downward and anterior facing convexly curved portion to form the ankle, a substantially anterior facing convexly curvilinear portion extending above the ankle to a substantially vertically oriented upper end forming the lower prosthetic part of a leg, wherein the shank has width in the frontal plane of the prosthetic foot which is greater than the thickness in the sagittal plane throughout the entire length of the shank such that the upper end during use of the prosthetic foot moves longitudinally with respect to the foot keel posteriorly in plantarflexion and anteriorly in dorsiflexion for storing and releasing energy to improve dynamic response of the prosthetic foot in force loading and unloading of the prosthetic foot; and using a posterior calf device on the prosthetic foot to store energy during force loading of the prosthetic foot and return the stored energy during force unloading to increase the kinetic power generated for propulsive force by the prosthetic foot in gait.

58. The method according to claim 57, wherein said device is a flexible strap which allows limited elastic extension of the strap with force loading of the prosthetic foot in gait.

59. The method according to claim 57, including forming a midfoot portion of the foot keel with a resilient longitudinal arch for storing and releasing energy during said gait to add to the kinetic power generated for propulsive force by the prosthetic foot in gait.

60. The method according to claim 59, including forming the longitudinal arch with a concavity having a medial aspect which is larger in radius than the lateral aspect.

61. A lower extremity prosthesis comprising:
a longitudinally extending foot keel;
a resilient, monolithically formed shank having a lower end connected to the foot keel and posteriorly terminating in a free end, an initially downward and anterior facing convexly curved portion of the shank extending upwardly from the foot keel to form an ankle joint area of the prosthesis, the shank extending upwardly in a substantially anterior facing convexly curvilinear manner above the ankle joint area to a substantially vertically oriented upper end to form a lower prosthetic part of a leg, to connect with a lower extremity prosthetic socket on a person's leg stump, wherein the width of the shank in the frontal plane of the prosthesis is greater than the thickness of the shank in the sagittal throughout the entire length of the shank such that the upper end is moveable longitudinally of the foot keel in response to force loading and unloading of the shank during use of the prosthesis; and
a device connected to an upper portion of the shank and a lower portion of the prosthesis to store energy during force loading of the prosthesis and return the stored energy during force unloading to increase the kinetic power generated for propulsive force by the prosthesis in gait.

62. The prosthesis according to claim 61, wherein the lower portion of the prosthesis to which the device is connected is a lower portion of the shank.

63. A lower extremity prosthesis comprising:
a longitudinally extending foot keel;
a resilient, monolithically formed shank having a lower end connected to the foot keel and posteriorly terminating in a free end, an initially downward and anterior facing convexly curved portion of the shank extending upwardly from the foot keel to form an ankle joint area of the prosthesis, the shank extending upwardly in a substantially anterior facing convexly curvilinear manner above the ankle joint area to a substantially vertical upper end above the ankle joint area to connect with a lower extremity prosthetic socket on a person's leg stump, the width of the shank in the frontal plane of the prosthesis being greater than the thickness of the shank in the sagittal plane throughout the entire length of the shank such that the upper end is moveable longitudinally of the foot keel in response to force loading and unloading of the shank during use of the prosthesis; and
a device connected to an upper portion of the shank and a lower portion of the prosthesis to control the extent of longitudinal motion of the upper end of the shank with respect to the foot keel during use of the prosthesis.

64. The prosthesis according to claim 63, wherein the lower portion of the prosthesis to which the device is connected is a lower portion of the shank.

65. A method of generating kinetic power for propulsive force in a resilient lower extremity prosthesis including an upwardly arched foot, and a monolithically formed resilient member having a lower end connected with the foot and posteriorly terminating in a free end, the member extending upwardly from the foot by way of an initially downward and anterior facing continuous convexly curved surface to form an ankle of the prosthesis and extending upwardly in a substantially anterior facing convexly curvilinear manner above the ankle to a substantially vertically oriented upper end forming a shank above the ankle, wherein the width of the resilient member in the frontal plane if the prosthesis is greater than the thickness of the member in the sagittal plane throughout the entire length of the member method comprising:

expanding a plurality of foot and shank concavities of the resilient prosthesis during midstance to late midstance force loading of the prosthesis in the active propulsion phase of a person's gait to store energy in the prosthesis;

releasing said stored energy in the later stages of stance-phase of gait to add to the propulsion of a trailing limb and person's body;

wherein during said force loading of the prosthesis in the active propulsion phase of gait storing additional energy in a posterior calf device connected between upper and lower portions of the prosthesis, and in said later stages of stance-phase of gait, releasing said additional energy to further add to the propulsion of the person's trailing limb and body.

66. The method according to claim 65, wherein said expanding includes expanding a concavity formed by an upwardly arched midfoot of said foot.

67. The method according to claim 65, wherein said expanding includes expanding a posterior facing concavity of said shank.

68. The method according to claim 65, wherein said expanding includes expanding a concavity formed by an anterior facing convexly curved portion of said resilient member.

* * * * *